US006899882B1

(12) United States Patent
Ferrara et al.

(10) Patent No.: US 6,899,882 B1
(45) Date of Patent: May 31, 2005

(54) ENDOTHELIAL CELL GROWTH FACTOR METHODS OF ISOLATION AND EXPRESSION

(75) Inventors: Napoleone Ferrara, Belvedere, CA (US); Denis Gospodarowicz, San Francisco, CA (US); Jean Plouet, Paris (FR)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/473,276

(22) Filed: Jun. 6, 1995

Related U.S. Application Data

(63) Continuation of application No. 08/158,027, filed on Nov. 26, 1993, now abandoned, which is a continuation of application No. 07/360,235, filed on Jun. 1, 1989, now abandoned, which is a continuation-in-part of application No. 07/346,165, filed on May 2, 1989, now abandoned, which is a continuation-in-part of application No. 07/328,181, filed on Mar. 24, 1989, now abandoned.

(51) Int. Cl.[7] ............................................. A61K 38/18
(52) U.S. Cl. ......................... 424/198.1; 514/2; 530/399
(58) Field of Search ................................ 530/350, 399; 514/2; 424/198.1

(56) References Cited

U.S. PATENT DOCUMENTS

| | | | | |
|---|---|---|---|---|
| 4,456,550 A | * | 6/1984 | Dvorak et al. ............ | 424/158.1 |
| 4,670,394 A | | 6/1987 | Pollard et al. ............. | 435/240 |
| 4,721,672 A | | 1/1988 | Vallee et al. ................. | 435/70 |
| 4,738,927 A | | 4/1988 | Taniguchi et al. .......... | 435/243 |
| 4,783,412 A | | 11/1988 | Bell ........................ | 435/240.1 |
| 4,801,542 A | | 1/1989 | Murray et al. ............ | 435/172.3 |
| 5,008,196 A | * | 4/1991 | Connolly et al. ........ | 435/240.2 |
| 5,073,492 A | * | 12/1991 | Chen et al. .............. | 435/240.2 |

FOREIGN PATENT DOCUMENTS

| | | |
|---|---|---|
| WO | WO84/021 | 6/1984 |
| WO | 0370989 | 6/1990 |
| WO | WO9102058 | 2/1991 |

OTHER PUBLICATIONS

Ferrara et al. Proc. Natl. Acad. Sci. USA 84, 5773–5777, 1987.*
Senger et al. (1983) Science 219, 983–985.*
Criscuolo et al. (1988) J. Neurosurg. 69, 254–262.*
D.W. Leung, Science, vol. 246, p. 1306, (Dec. 8, 1989).
P.J. Keck, et al. *Science*, vol. 246, p. 1309, (Dec. 8, 1989).
G.E. Lemke, et al. *Journal of Neuroscience*, vol. 4 No. 1, p. 75 (Jan. 1984).
N. Ferrara, et al., *Biochemical and Biophysical Research Communications*, vol. 161, No. 2, p. 851 (Jun. 15, 1989).
D. Gospodarowicz, et al. *Biochemistry*, vol. 86 p. 882 (1989).
N. Ling, et al. *Biochemistry*, vol. 82, p. 7217 Nov. 1985).
N. Ueno, et al., *Biochemistry* vol. 84, p. 8282 (Dec. 1987).
S. Shimasaki, et al., *Biochemical and Research Communications*, vol. 152, p. 717, (Apr. 29, 1988).
D. M. Robertson et al. *Biochemical Biophysical Research Communications*, vol. 149, No. 2, p. 744 (Dec. 16, 1987).
D.R. Senger, et al. *Cancer Research*, vol. 46 p. 5629, (Nov. 1986).
D.T. Connolly, et al., J. Clinical Investigation, vol. 84 p. 1470 (Nov. 1989).
D.T. Connelly, et al., *Journal of Biological Chemistry* vol. 264, #44, p. 20017 (1989).
F. Ishikawa, et al., *Nature*, vol. 338 p. 557 (Apr. 1989).
J.S. Rubin, et al. *Proc. Natl. Acad. Sci, U.S.A.*, vol. 86 p. 802, (Feb. 1989).
Burgess et al. J. Biol. Chem. 260(21), p. 11389–11392, 1985.
Winkles et al. Proc. Natl. Acad. Sci. USA 84, p. 7124–7128, 1987.
Tashiro et al. Proc. Natl. Acad. Sci. USA 87, 3200–3204, 1990.
Gimencz–Gallego et al. BBRC. 138(2), 611–617, 1986.
Lobb et al. J. Biol. Chem. 261(4), 1924–1928, 1986.
G. Conn et al., "Purification of a glycoprotein vascular endothelial cell mitogen from a rat glioma–derived cell line", Proc. Nat. Acad. Sci. USA, vol. 87 (1990), pp. 1323–1327.
G. Conn, Amino acid and cDNA sequences of a vascular endothelial cell mitogen that is homologous t platelet–derived growth factor:, Proc. Nat. Acad. Sci., vol. 87 (1990), pp. 2628–2632.
D.R. Senger et al., "Purification of $NH_2$–Terminal Amino Acid Sequence of Guinea Pig Tumor–secreted Vascular Permeability Factor", Cancer Res., vol. 50 (1990), pp. 1774–1778.
N. Ferrara et al., The Vascular Endothelial Growth Factor Family of Polypeptides, *J. Cell Biochem.*, vol. 47 (1991), pp. 211–218.
C. de Vries et al., "The fms–Like Tyrosine Kinase, a Receptor for Vascular Endothelial Growth Fact r", Science, vol. 255 (1992), pp. 989–991.

(Continued)

*Primary Examiner*—Lorraine Spector
(74) *Attorney, Agent, or Firm*—Peters, Verny, Jones, Schmitt & Aston, LLP; Howard M. Peters

(57) ABSTRACT

A novel growth factor specific for vascular endothelial cells has been identified in conditioned medium of bovine pituitary derived folliculo stellate cells. This factor, named folliculo stellate derived growth facto (FSdGF) or vascular endothelial growth factor (VEGF), was purified to homogeneity by a combination of heparin sepharose affinity chromatography, Bio Gel P-60 exclusion chromatography, Mono S ion exchange chromatography and hydrophobic chromatography on a C4 reverse phase HPLC column. The factor is also found in the murine AtT-20 cell line.

15 Claims, 20 Drawing Sheets

OTHER PUBLICATIONS

G. Beck et al., "Isolation and Characterization of a Vascular Permeability Factor from Stimulated U937 Cells", J. Leukocyte Bio. vol. 42:5 (1987), p. 568.

J.N. Bruce et al., "Vascular Permeability induced by protein product of malignant brain tumors: inhibition by dexamethasone", J. Neurosurg., vol. 67 (1987), pp. 880–884.

G. Gospodarowicz et al., "Isolation and characterization of a vascular endothelial cell mitogen produced by pituitary–derived folliculo stellate cells", stellate cells, Proc. Nat. Acad. Sci., vol. 86 (1989), pp. 7311–7315.

J. Plouet et al., Isolation and characterization of a newly identified endothelial cell mitogen produced by AtT–20 cells, EMBO J., vol. 8:12 (1989), pp. 3801–3806.

Edmund Tischer et al., "Vascular Endothelial Growth Factor: A New Member of the Platelet–Derived Growth Factor Gene Family," Biochemical & Biophysical Research Communications, vol. 165(3), pp. 1198–1206.

* cited by examiner

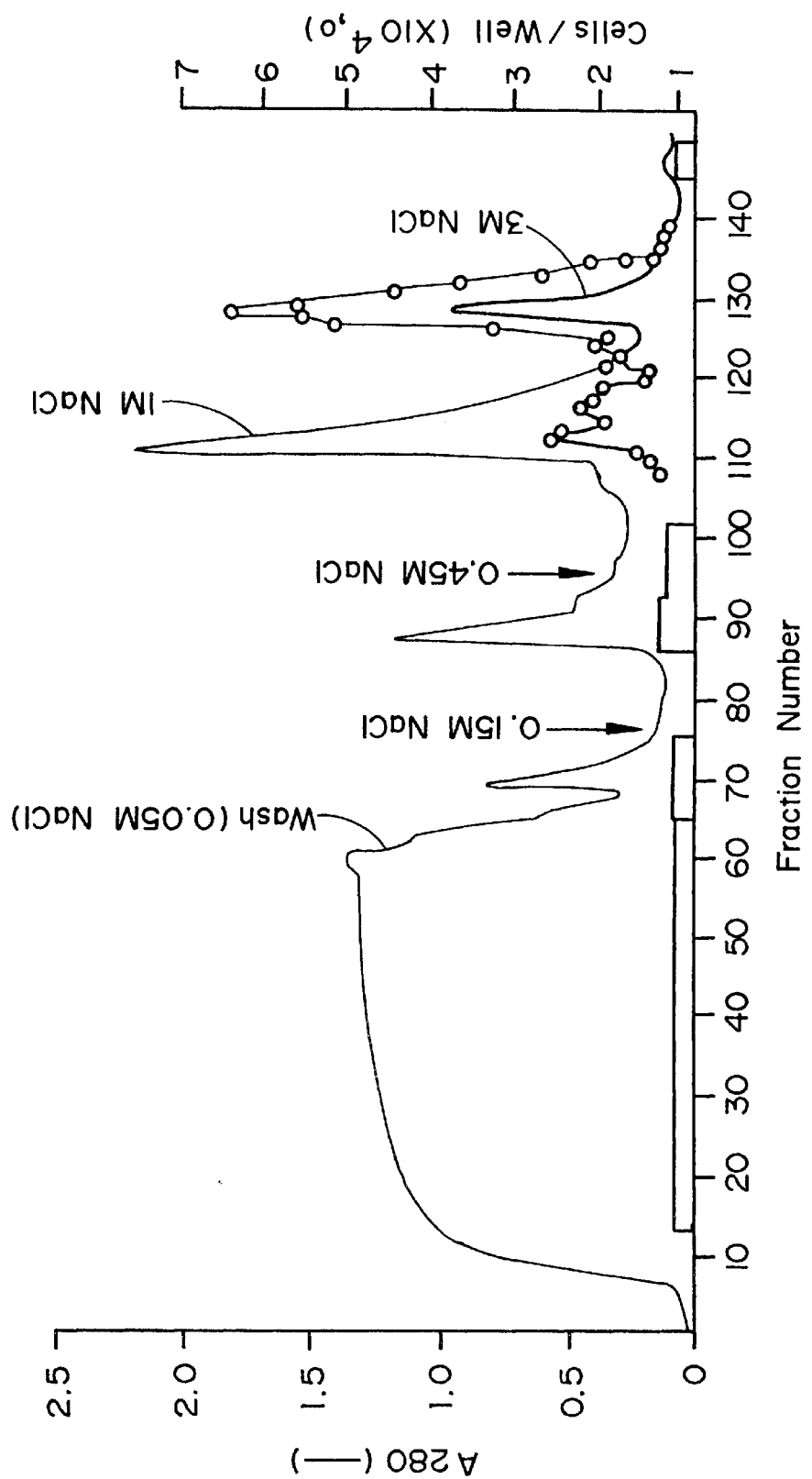
FIG._1A

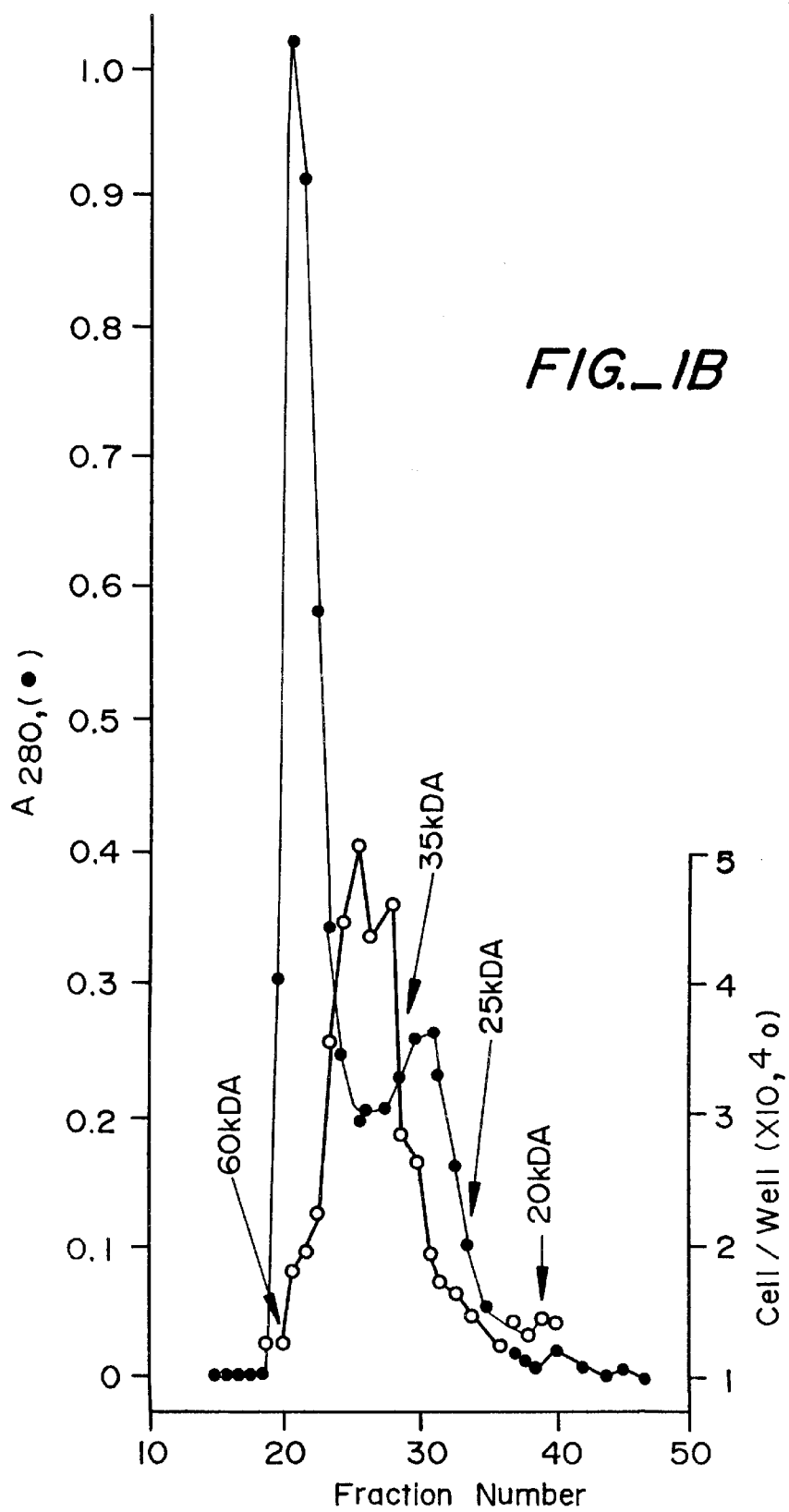

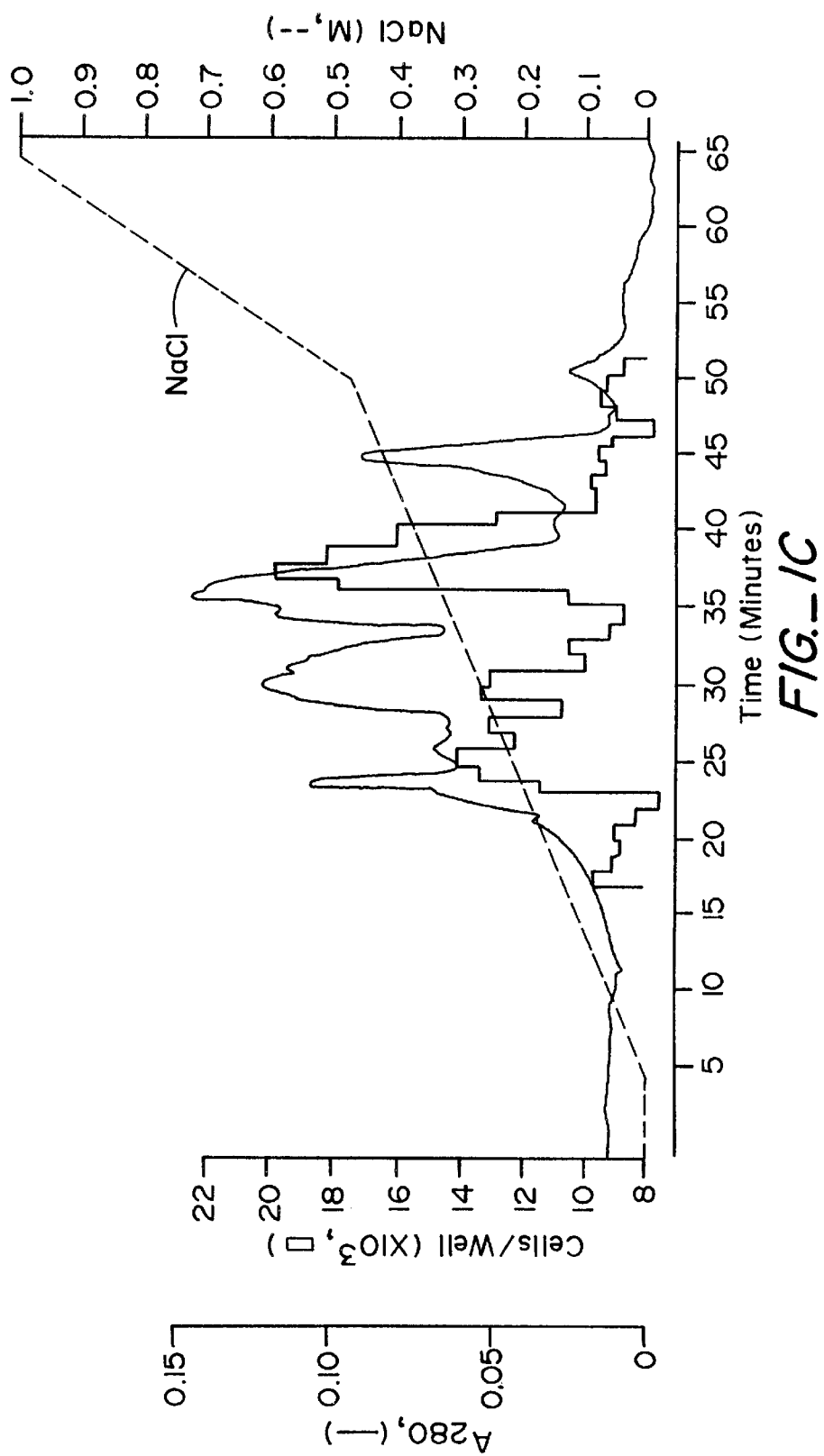
FIG._1C

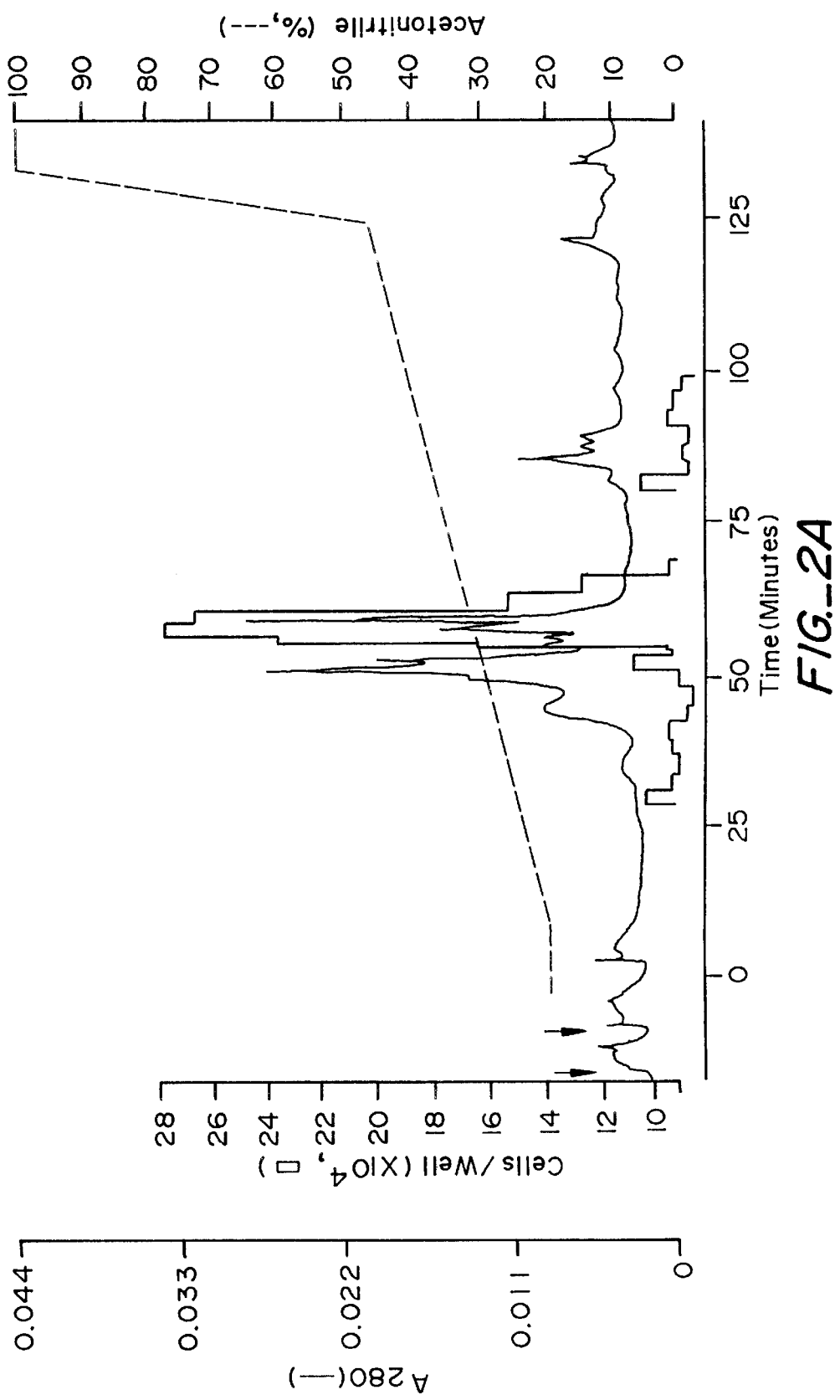
FIG._2A

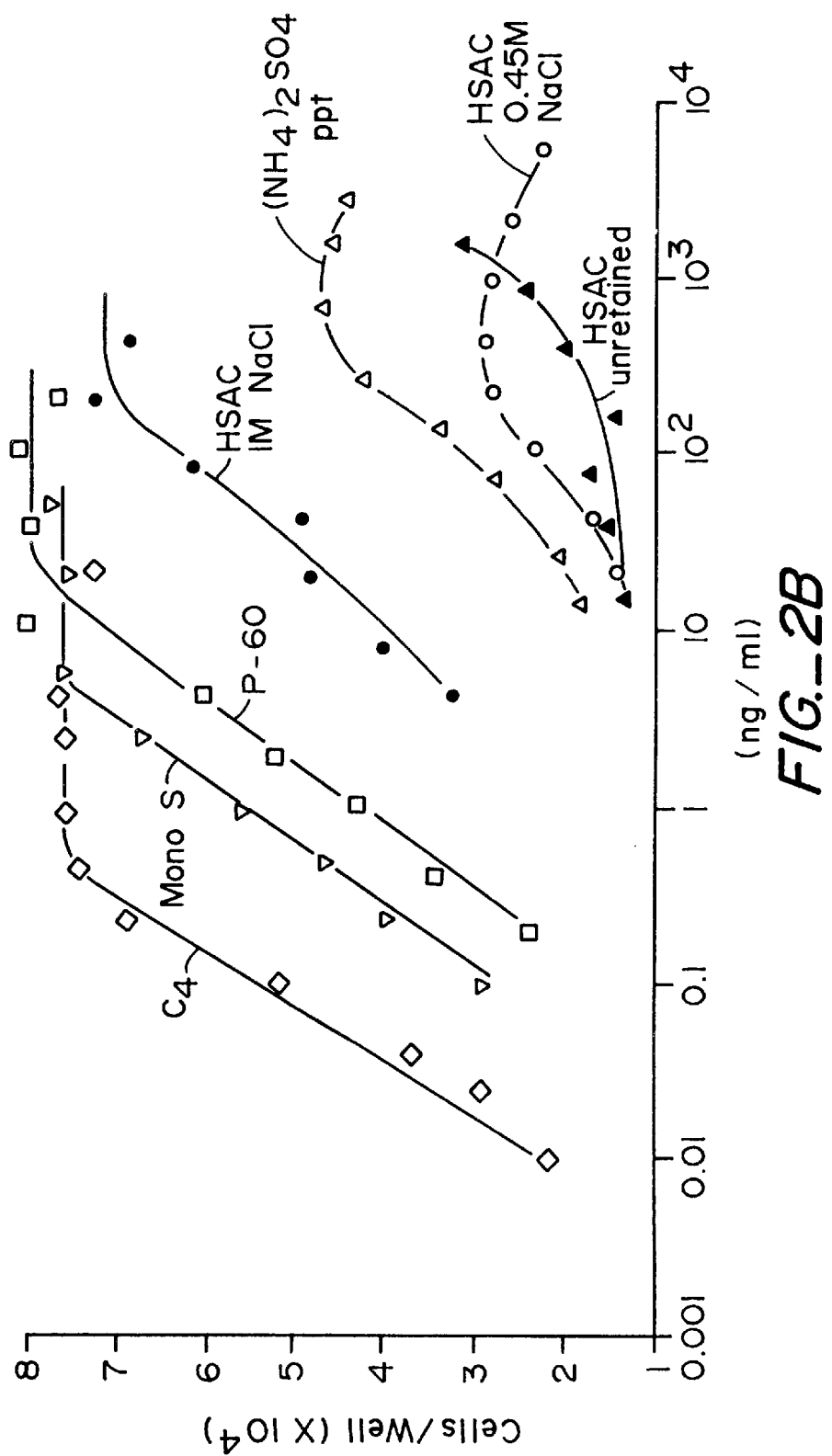
FIG._2B

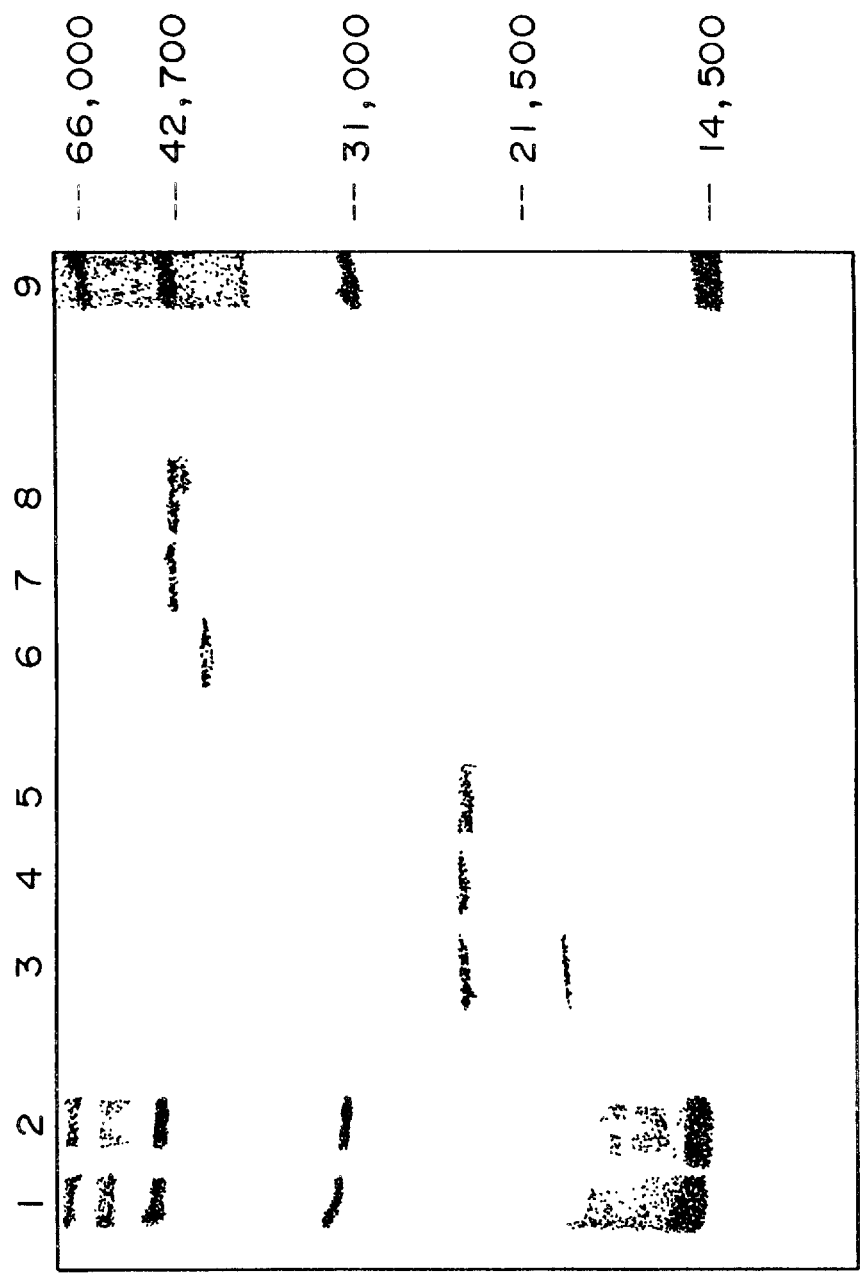
FIG._3

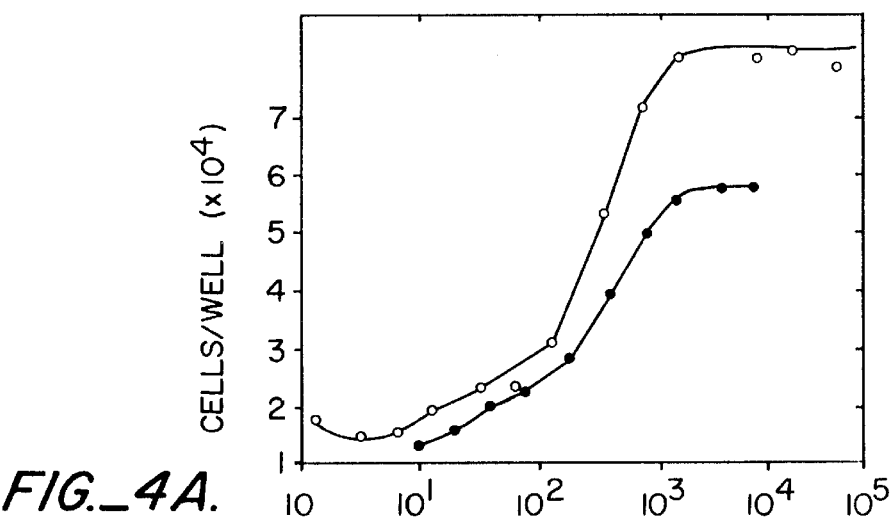
FIG._4A.
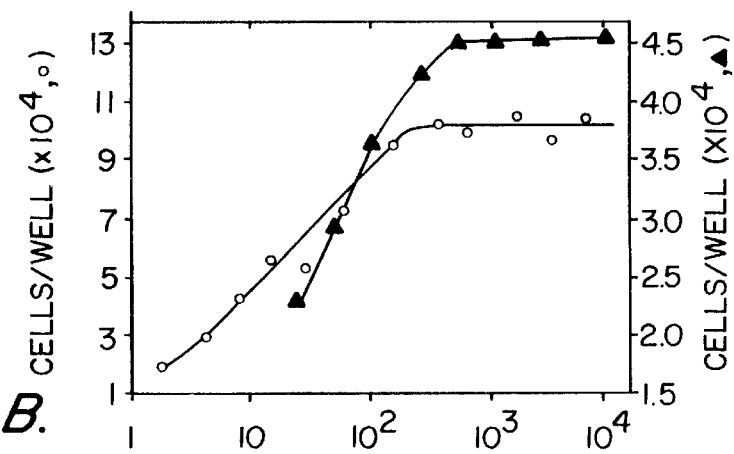
FIG._4B.
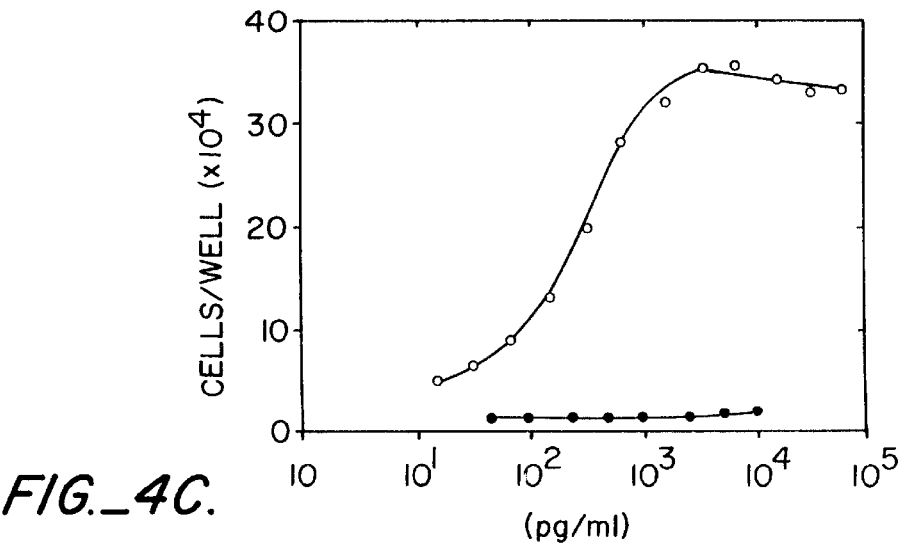
FIG._4C.

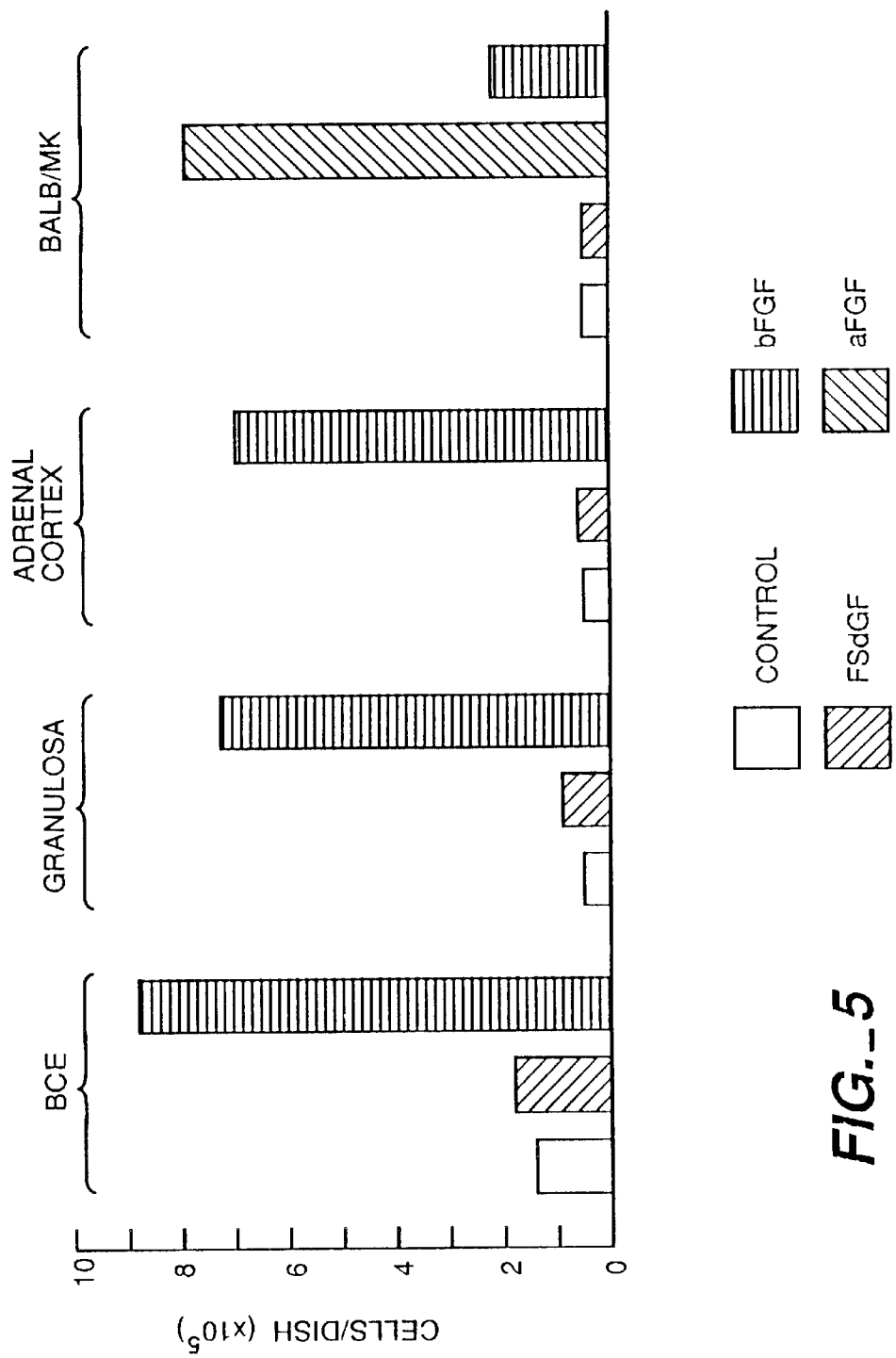
FIG._5

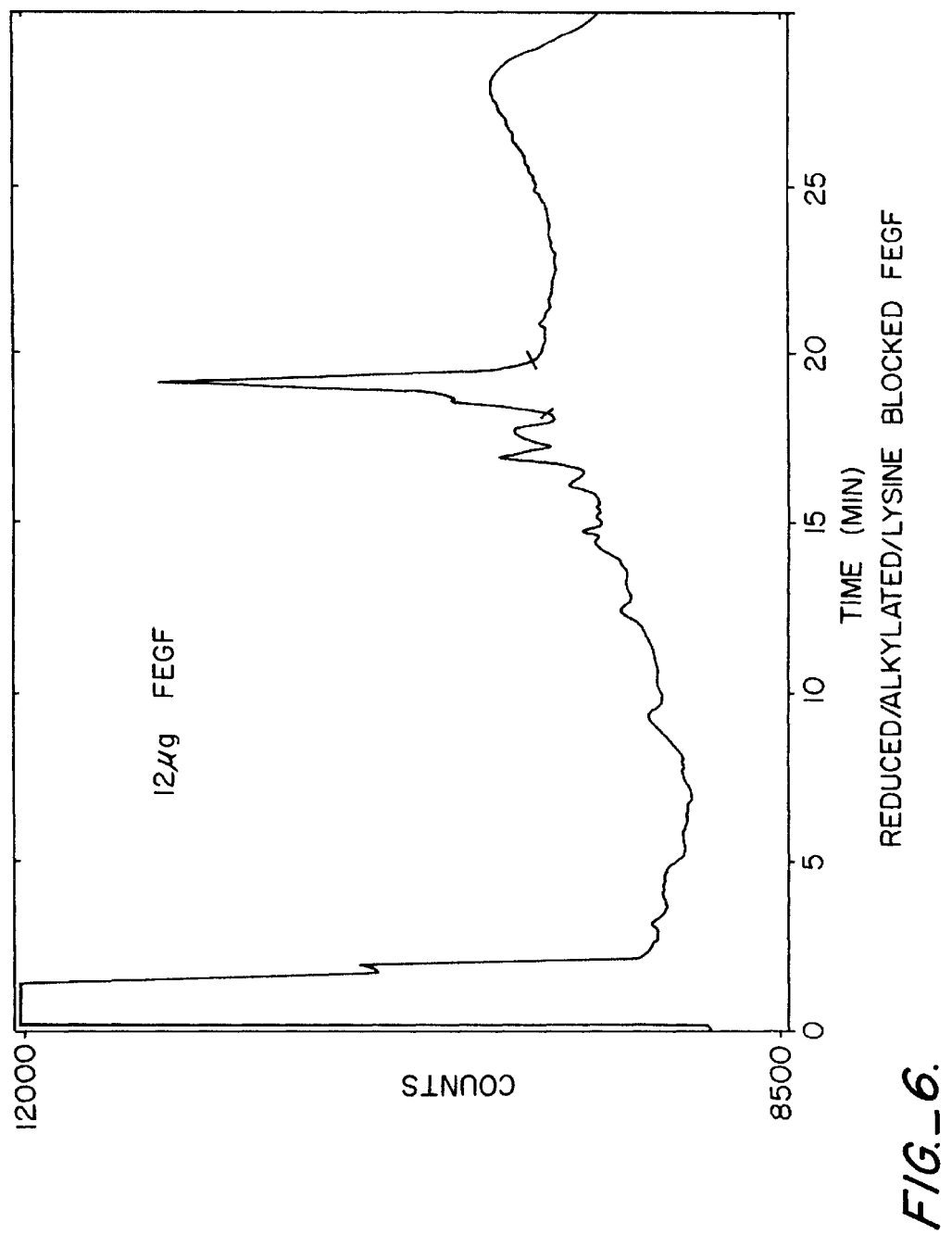
FIG._6.

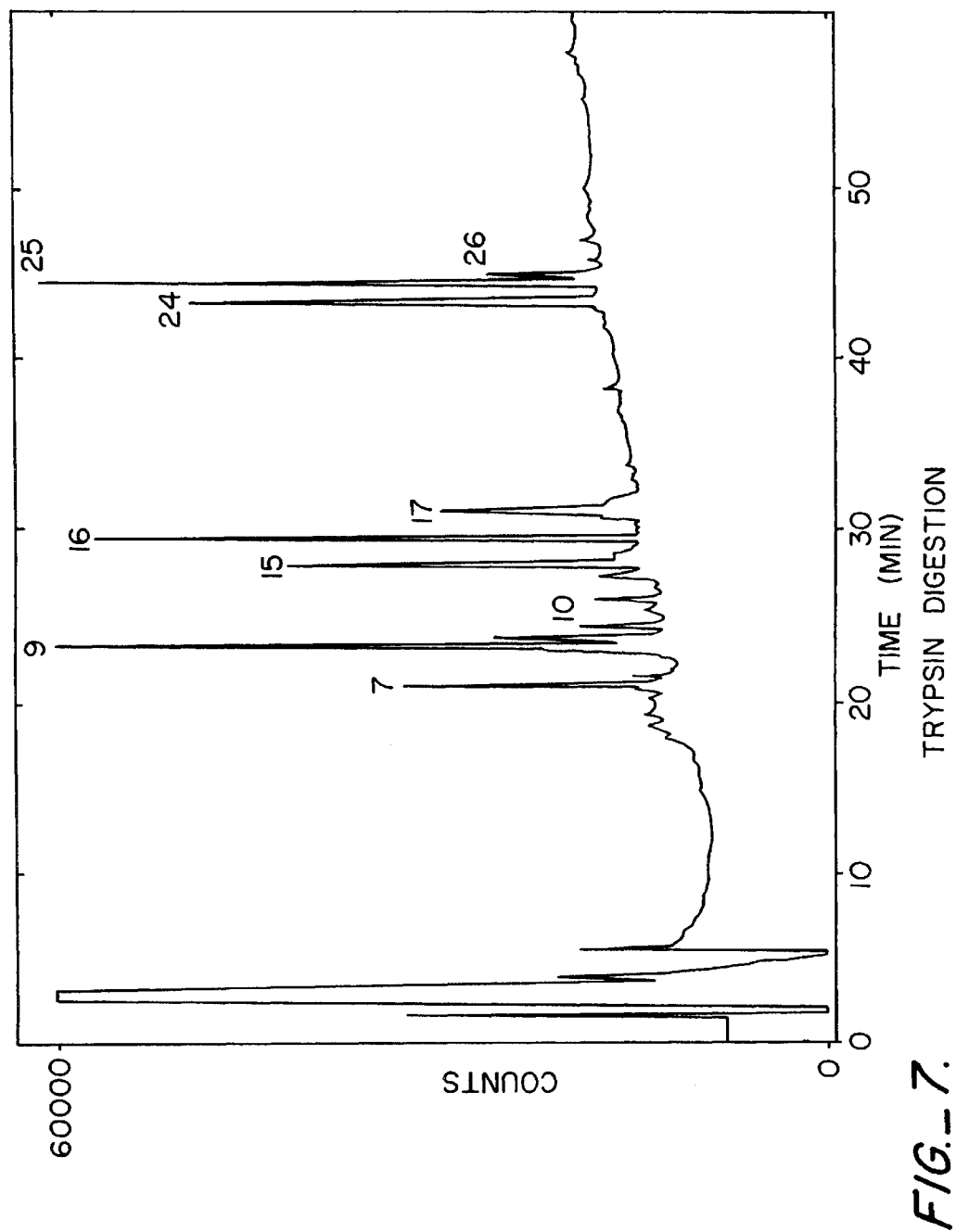
FIG._7.

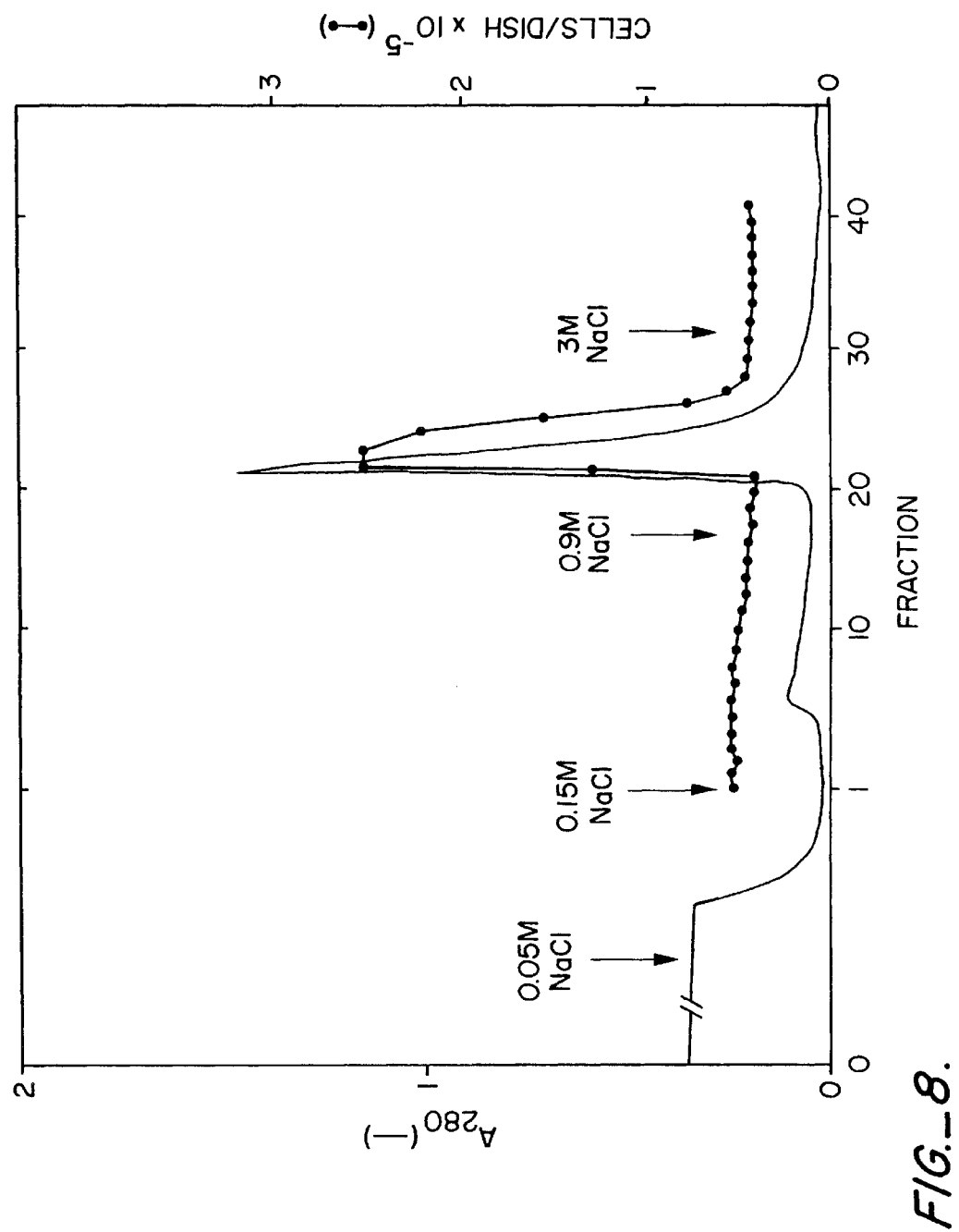
FIG._8.

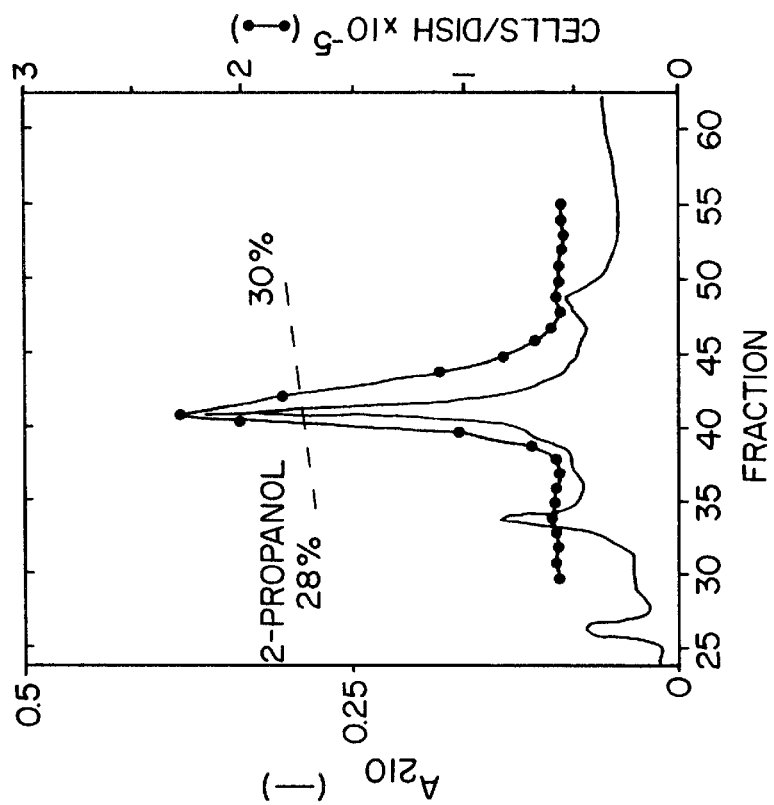
FIG._9B.
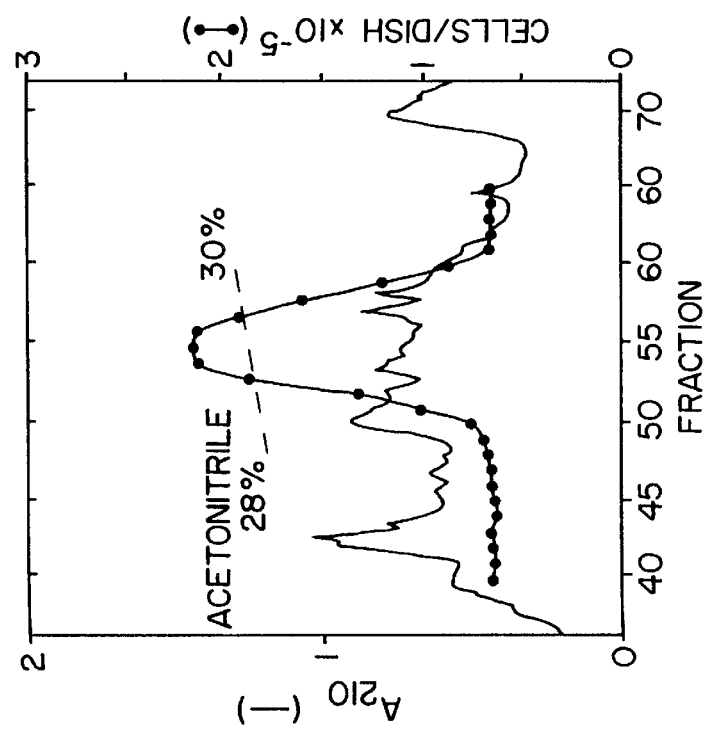
FIG._9A.

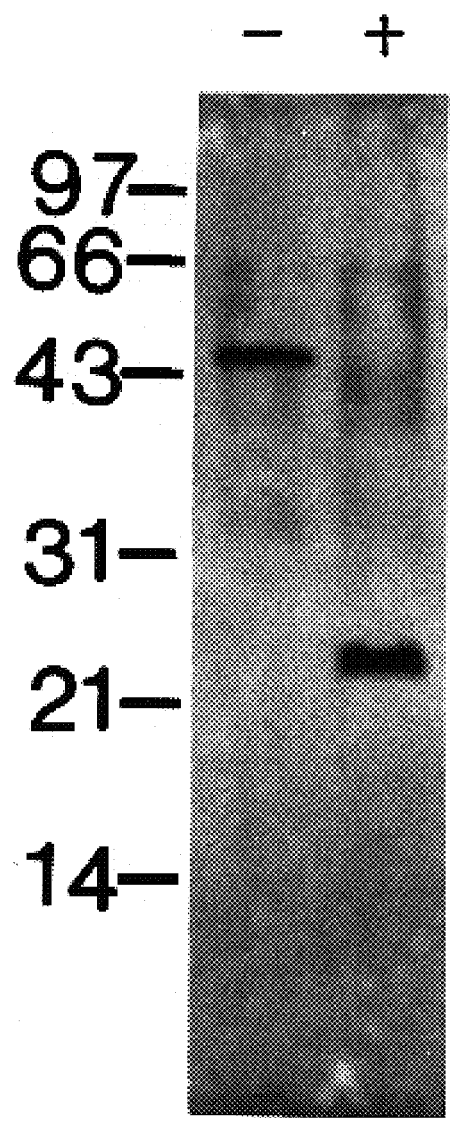
FIG._10

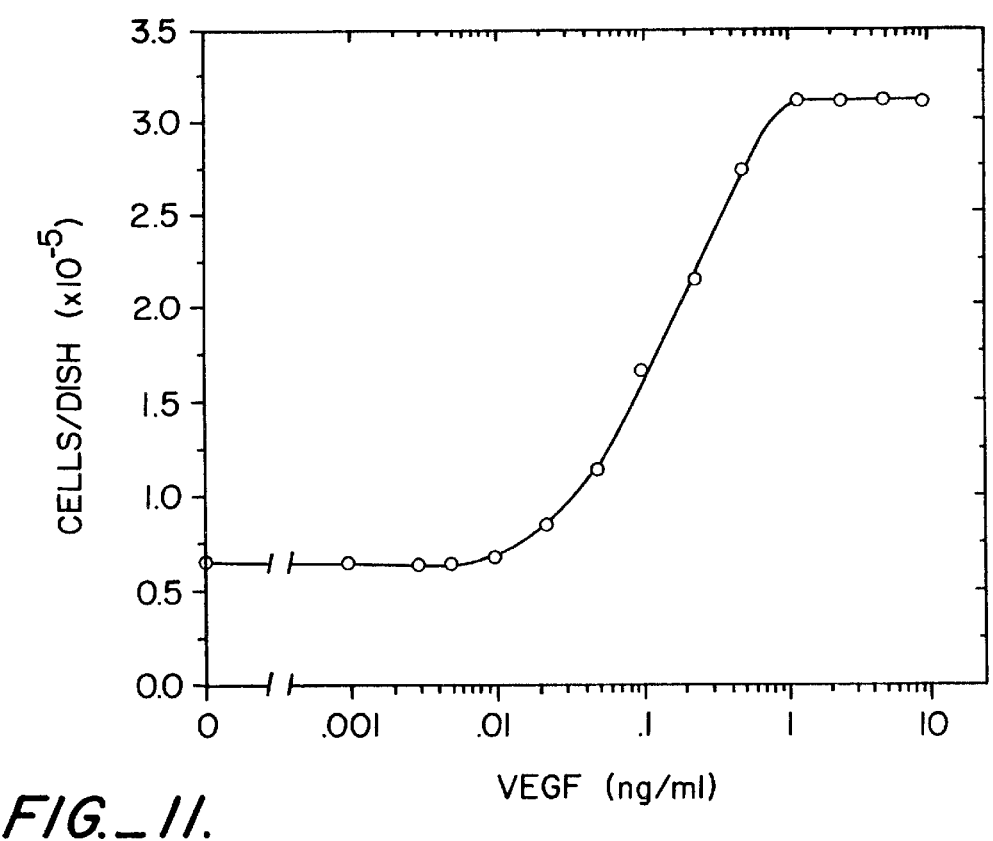
FIG._11.

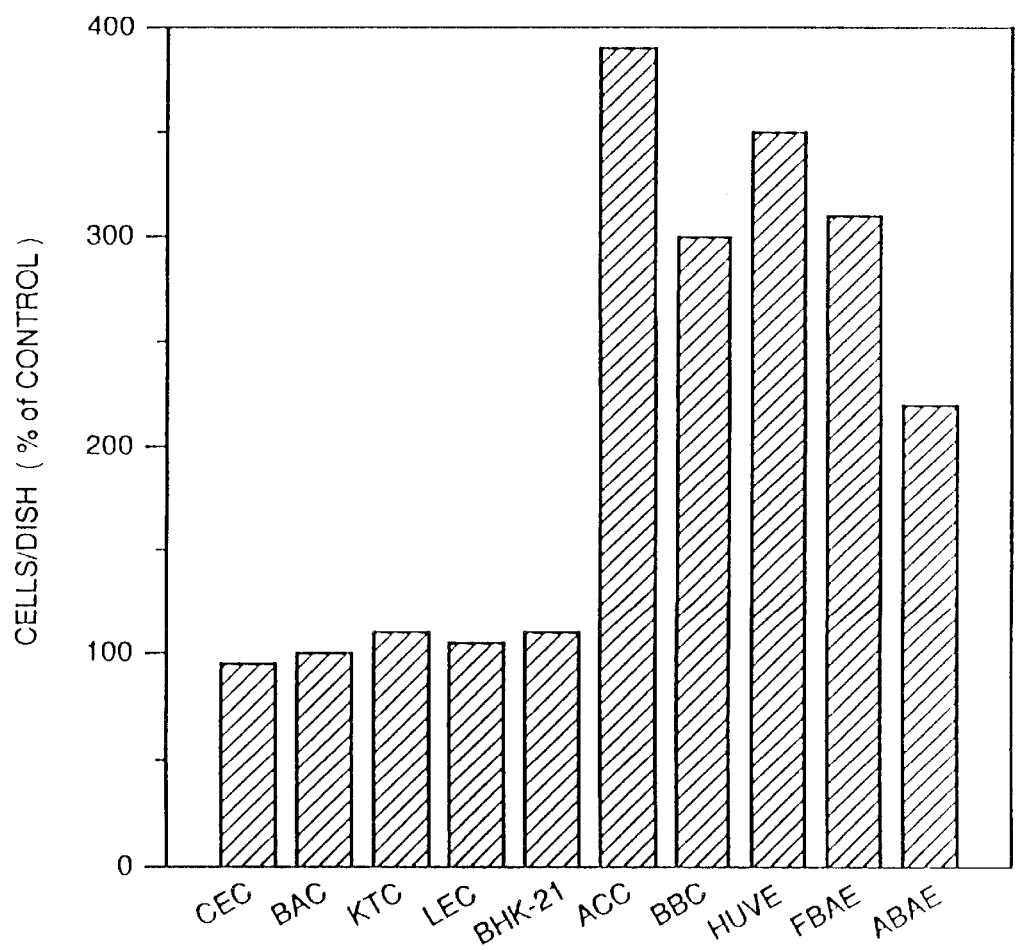
FIG._12

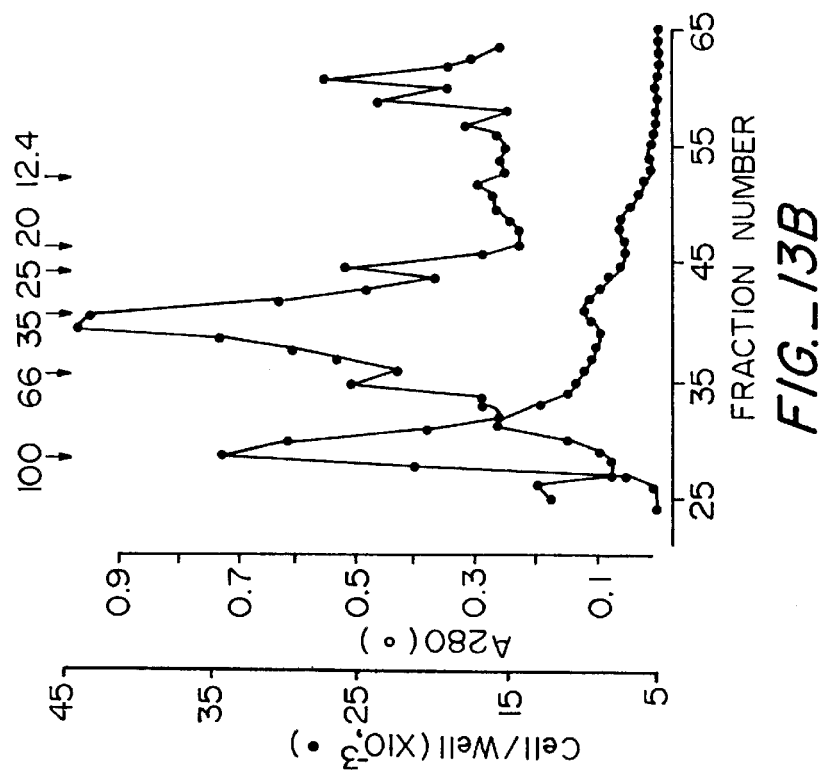
FIG._13B
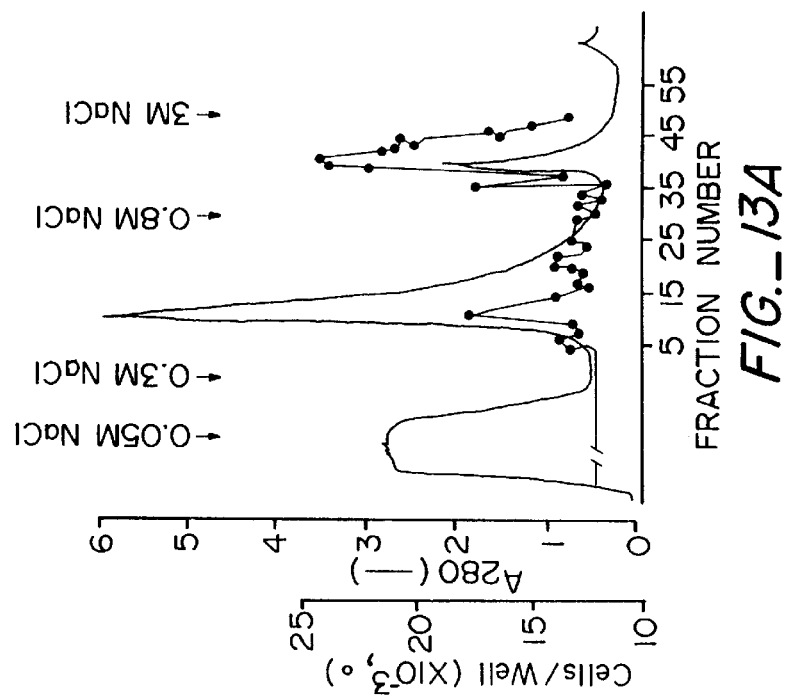
FIG._13A

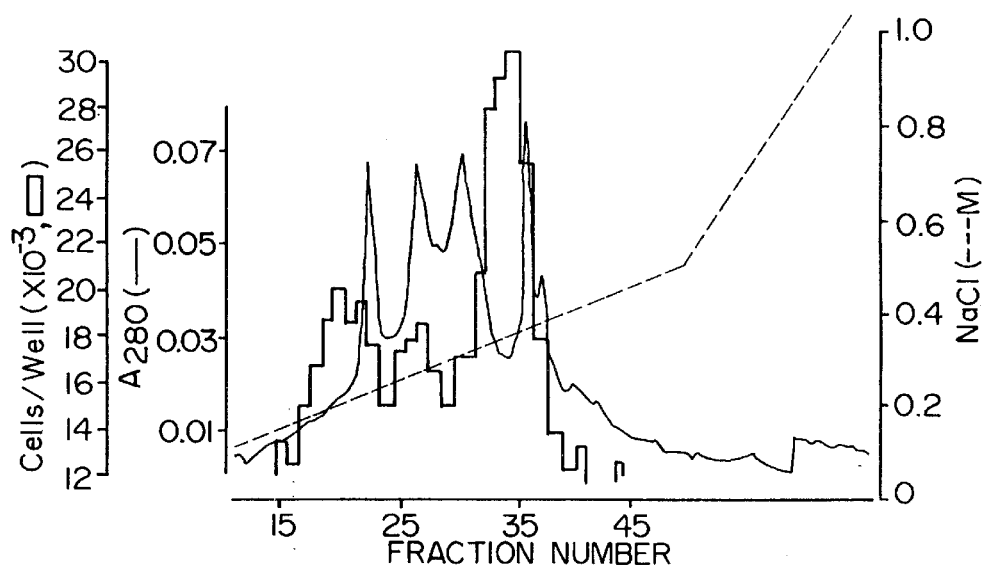
FIG._13C
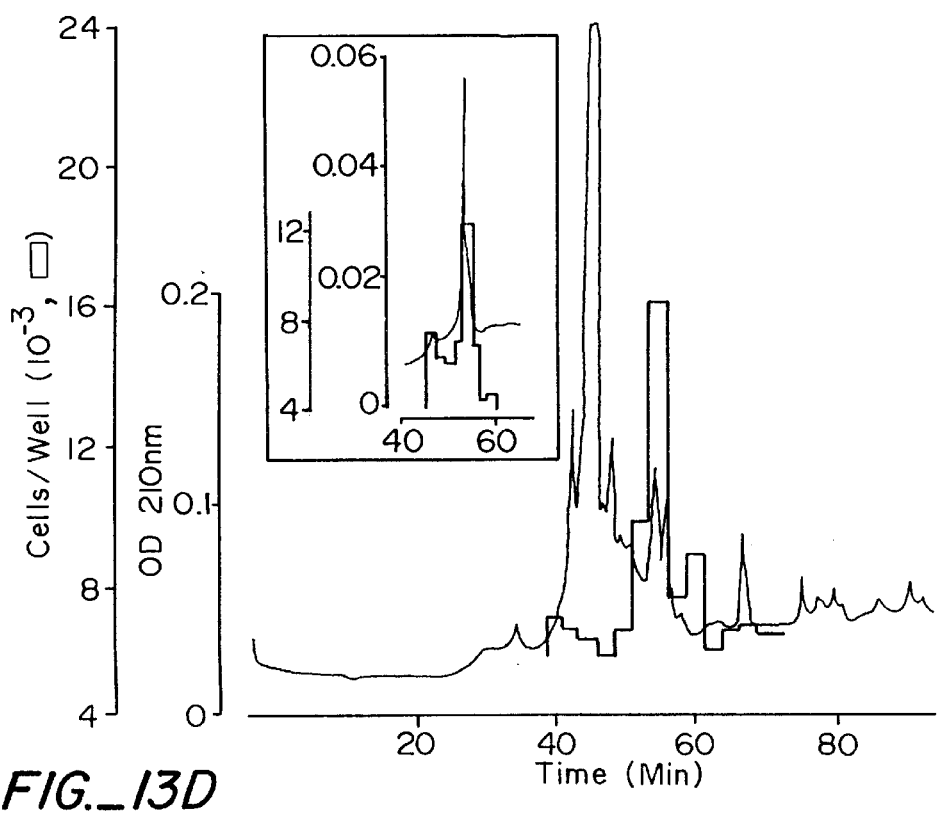
FIG._13D

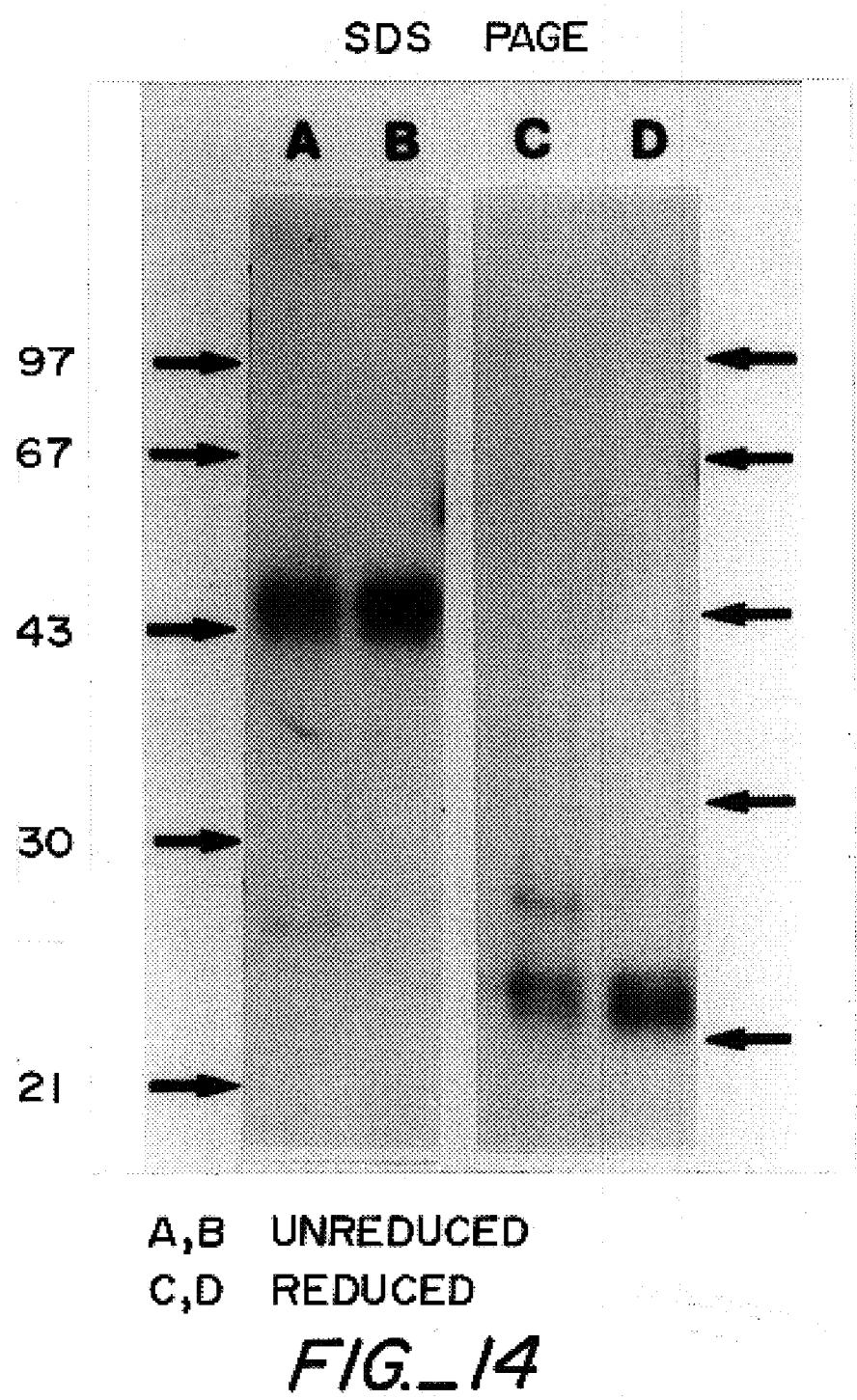
FIG._14

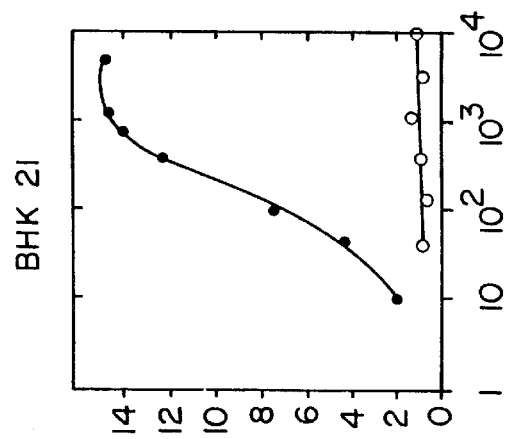
FIG._15C.
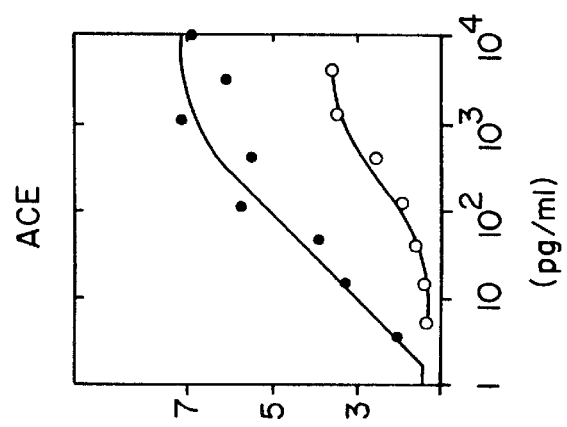
FIG._15B.
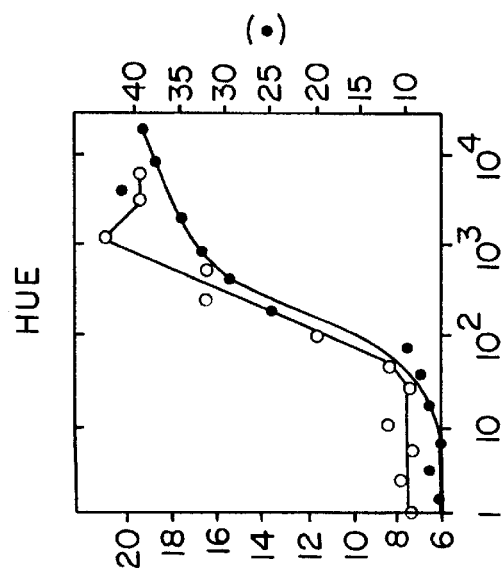
FIG._15A.

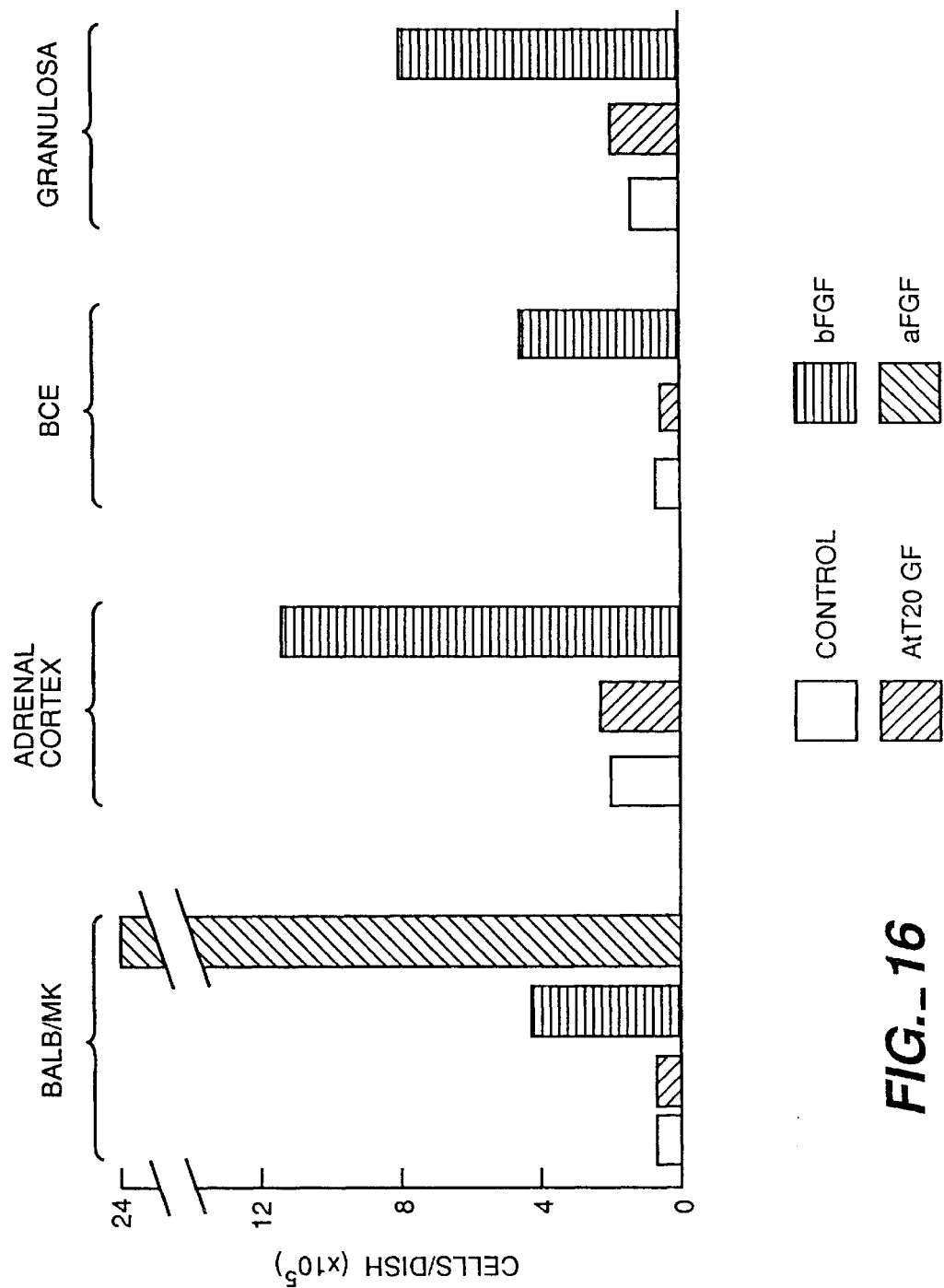
FIG._16

ENDOTHELIAL CELL GROWTH FACTOR METHODS OF ISOLATION AND EXPRESSION

This is a continuation of application, Ser. No 08/158,027, filed Nov. 26, 1993 now abandoned, which is a continuation of U.S. Ser. No. 07/360,235, filed Jun. 1, 1989, now abandoned, which is a continuation-in-part of U.S. Ser. 07/346,165, filed May 2, 1989, now abandoned, which is a continuation-in-part of U.S. Ser. No. 07/328,181, filed Mar. 24, 1989, now abandoned.

The present application is a continuation-in-part of pending U.S. patent application Ser. No. 346,165, filed May 2, 1989, which is a continuation-in-part of pending U.S. patent application Ser. No. 328,181, filed Mar. 24, 1989, which are both incorporated by reference in its entirety.

ORIGIN OF THE INVENTION

The present invention was made with Government support in part on U.S. National Institute of Health Grant Nos. 5ROIEY 02186; 5ROIHL 20197; and HD 08035 awarded by the Department of Health and Human Services to the University of California at San Francisco, Calif. The U.S. Government has certain rights in this invention.

BACKGROUND OF INVENTION

1. Field of the Invention

The present invention relates to a novel growth factor for vascular endothelial cells identified in media condition of cultured bovine pituitary follicular cells and of murine tumor cells. The invention also relates to isolation and purification of the growth factor.

2. Description of the Problem and Related Art

Numerical references in parenthesis in the text refer to the publications listed below in the Reference Section.

Angiogenesis is a multi-step phenomenon which involves capillary endothelial cell proliferation, migration and tissue infiltration (1). It plays a central role in a variety of physiological and pathological processes such as embryonic development, wound healing, atherosclerosis and tumor growth (1,2). Several factors induce angiogenesis have recently been isolated and characterized. Among these are the acidic and basic form of fibroblast growth factor (FGF), both capable of stimulating capillary endothelial cell growth in vitro as well as being chemotactic for that cell type (2). In addition, both acidic and basic FGF stimulate collagenase activity and plasminogen activator production while blocking the activity of plasminogen inhibitor (3,4). These enzymes are involved in the breakdown of the capillary basement membrane, an event required in order for angiogenesis to take place (1). Other growth factors such as tumor necrosis factor alpha (TNFα), transforming growth factor beta (TGF), transforming growth factor alpha (TGFα), and epidermal growth factor (EGF) are also angiogenic in vivo (5–8). However, with the exception of TGFα and EGF at high concentrations (7), these growth factors are not mitogenic for capillary endothelial cells (5,6); their action on the angiogenic process is therefore probably indirect, resulting from such activities as the attraction of macrophages by chemotaxis (9,10) which in turn release direct angiogenic factor(s), one of which could be basic FGF (11).

A number of growth factors, such as acidic and basic FGF, PDGF and EGF, are broadly mitogenic for a number of cell types. This broad mitogenicity is desirable in many types of wound healing applications. There are, however, specific types of wound healing applications in which it would be more desirable to employ growth factors having more cell-specific mitogenic activity. For example, following vascular graft surgery or balloon angioplasty, it would be highly desirable to employ a wound healing agent incorporating mitogenic factor having mitogenic activity that is highly specific for vascular endothelial cells. At present, no highly suitable mitogenic factor exists for this type of application.

In the course of our studies on the localization of basic FGF in various tissues, it was observed that, in the pituitary gland, folliculo stellate cells are the main producers of bFGF (18). Although the medium conditioned by those cells was found to be strongly mitogenic for capillary endothelial cells, little if any bFGF is present in it, thus suggesting that, in addition to synthesizing bFGF, these cells are also capable of producing another endothelial cell mitogen. To date, however, this mitogenic activity has not been purified or characterized.

The following publications are of interest as background in this art.

1. Folkman, J. (1986) *Cancer Res.* 46, 467–473.
2. Gospodarowicz, D., et al. (1987) *Endocrine Reviews* 8, 95–114.
3. Saksela, O., et al. (1987) *J. Cell Biol.* 107, 957–962.
4. Montesano, R., et al. (1986) *Proc. Natl. Acad. Sci. U.S.A.* 83, 7297–7301.
5. Frater-Schroeder, M. (1987) *Proc. Natl. Acad. Sci. U.S.A.* 84, 5277–5281.
6. Sporn, M. B., et al. (1986) *Proc. Natl. Acad. Sci, U.S.A.* 83, 4167–4272.
7. Schreiber, A. B., et al. (1986) *Science* 232, 1250–1253.
8. Gospodarowicz, D., et al. (1979) *Expt. Eye Res.* 28, 501–514.
9. Leibovich, S., et al. (1987) *Nature* 329, 630–632.
10. Wahl, S. M., et al. (1987) *Proc. Natl. Acad. Sci. U.S.A.* 84, 5788–5792.
11. Baird, A., et al. (1985) *Biochem. Biophys. Res. Commun.* 126, 358–363.
12. Abraham, J. A., et al. (1986) *Science*, 233, 545–547.
13. Jaye, M., et al. (1985) *Science* 233, 541–545.
14. Schweigerer, L., et al. (1987) *Nature*, 325, 257–259.
15. Moscatelli, D., et al. (1986) *J. Cell. Physiol.* 129, 273–276.
16. Vlodavsky, I., et al. (1987) *Proc. Natl. Acad. Sci. U.S.A.* 84, 2292–2296.
17. Ferrara, N., et al. (1987) *Proc. Natl. Acad. Sci. U.S.A.* 84, 5773–5777.
18. Gospodarowicz, D., et al. (1984) *Proc. Natl. Acad. Sci. U.S.A.* 81, 6963, 6967.
19. Gospodarowicz, D., et al. (1988) *Europ. J. Cell. Biol.*, 46, 144–151.
20. Ferrara, N., et al. (1986) *Methods Enzymol.* 124, 235–253.
21. Gospodarowicz, D., et al. (1983) *J. Cell. Biol.* 7, 1677–1685.
22. Gospodarowicz, D., et al. (1986) *J. Cell. Physiol.*, 127, 121–136.
23. Gospodarowicz, D., et al. (1977) *Endocrinology* 100, 1108–1120.
24. Gospodarowicz, D., et al. (1977) *Endocrinology* 100, 1080–1089.
25. Gospodarowicz, D., et al. (1977) *Ext. Eye. Res.* 25, 75–89.
26. Neufeld, G., et al. (1986) *Regulatory Peptides* 13, 293–305.
27. Weissman, B. E., et al. (1983) *Cell* 32, 599–606.
28. McConahey, P., et al. (1966) *Int. Arch. Allergy* 29, 185–189.

29. Laemmli, U. K. (1970) *Nature*, (London) 227, 680–685.
30. Klagsburn, M., et al. Proc. Natl. Sci. U.S.A. 82, 805–809.
31. Gospodarowicz, D., (1987) *Methods Enzymol.* 147, 106–119.
32. Kudlow, J. E., et al. (1988) In Biology of growth factor. *Adv. in Exptl. Med. and Biol.* Pelnum Press New York 234, 105–126.
33. Frater-Schroder, M., et al. (1986) *Biochem. Biophys. Res. Commun.* 137, 295–302.
34. Baird, A., et al. (1986) *Biochem. Biophys. Res. Commun.* 138, 476–482.
35. Lipman, D. G., et al. (1985) *Science* (Wash., D.C.) 227, 1435–1441.
36. Rubin, J. S., et al. (1989) *Proc. Natl. Acad. Sci. U.S.A.* 86, 803–806.
37. Miyazono, K., et al. (1987) *J. Biol. Chem.*, 262, 4098–4103.
38. Farquhar, M. G., et al. In The Anterior Pituitary Gland (Tixier Vidal A., and Farquhar M. G. eds.) Acad. Press New York 1975, pp 82–102.
39. Gon, G. Shirasawa, et al. (1987) *Anat. Rec.* 217, 371–384.
40. Carpenter, G., et al. (1985) *Anal. Biochem.* 153, 279–282.
41. Ferrara, N., et al. (1987) *Am. J. Physiol.* 252, E304–312.
42. Ferrara, N., et al. (1988) *Biochem. Biophys. Res. Comm.*, 157, 1376–1382.
43. Abraham, J., et al. (1986) *EMBO J.*, 5, 2523–2529.
44. Water, P., et al. (1981) *J. Cell Biol.*, 91, 557–561.
45. Klagsburn, M., et al. (1986) *Proc. Natl. Acad. Sci. USA,* 83, 2448–2452.
46. Neufeld, G., et al. (1987) *Endocrinology,* 121, 597–602.
47. Schweigerer, L., et al. (1988) *Exp. Eye Res.,* 46(1), 71–80.
48. Schweigerer, L., et al. (1987) *Endocrinology,* 120, 796–802.
49. Shing, Y., et al. (1984), *Science* 223, 1296–1299.
50. Jaffe, E. A., et al. (1972) *J. Clin. Inv.* 51, 46a.
51. Folkman, J. (1982) *In: Pathobiology of the Endothelial Cell.* (Edited by Nossel, H. L., and Vogel, H. J.) pp 79–93, Academic Press, New York.
52. D'Amore, P. A., et al. (1981) *Proc. Natl. Acad. Sci. U.S.A,* 78, 3068–3072.
53. Pheel, D. M., et al. (1985) *In Vitro,* 16, 526–538.
54. Henzel, W. J., et al. (1987) *J. Chromatoaraph.,* 404, 41–52.
55. Morrissey, J. H. (1981) *Anal. Biochem.,* 117, 307–310.
56. Baird, A., et al. (1986) *Recent Prog. Hormone Res.,* 42, 143–186.
57. Roberts, R., et al. (1988) *Nature,* 332, 376–378.
58. Maciag, T., et al. (1984) *Science,* 225, 932–935.
59. Lobb, R. R., et al. (1984) *Biochemistry,* 23, 6295–6299.
60. Folkman, J., et al. (1987), *Science,* 235, 442–447.
61. Goustin, A. S., et al. (1986) *Cancer Res.,* 46, 1015–1029.
62. Bassett, D. L. (1943) *Am. J. Anat.,* 73, 251–259.
63. Gospodarowicz, D., et al. U.S. Pat. No. 4,785,079, issued Nov. 15, 1988.
64. B. Gumbiner, et al. (1981) *Proc. Natl. Acad. U.S.A.* 78, 318.
65. S. Blam, et al. (1988) *Oncogene* 3, 129.

All of the references and/or patents cited in this application are incorporated herein by reference.

Previously published research describes the culture of homogeneous populations of bovine pituitary follicular or folliculo-stellate cells (FC) (20) and subsequently characterized them as ion transport elements, possibly involved in the regulation of ion composition and osmolarity of the interstitial fluid in the adenohypophysial cell cords (41, 42). It is also reported that FC produce the angiogenic mitogen basic fibroblast growth factor (bFGF) (17).

The gene for bFGF (43), similarly to the gene for acidic fibroblast growth factor (aFGF) (13), does not code for a conventional signal peptide, required for the extracellular transport of proteins according to classic secretory pathways (44). Accordingly, the growth factor is not appreciably secreted in the medium (15,45) and responsive cell types are dependent on exogenous bFGF for optimal proliferation in culture, even though they may contain significant intracellular concentrations of mitogen (46,47,48).

It was initially observed, however, that the medium conditioned by bovine pituitary FC is mitogenic for adrenalcortex-derived capillary endothelial cells. Interestingly, these cells are responsive either to bFGF or aFGF but are not stimulated to proliferate by EGF, TGF alfa, TGF beta, PDGF, insulin or TNF (2). These observations led us to consider the possibility that an endothelial cell growth factor distinct from FGF and possibly any other known growth factor may be secreted by cultured FC.

The present invention describes the purification and biological characterizations of such a novel growth factor. Its unique N-terminal amino acid sequence, as well as its specificity for vascular endothelial cells, distinguishes it from any previously described growth factor.

SUMMARY OF THE INVENTION

In accordance with the present invention, there is provided a novel growth factor in isolated form, that is, unaccompanied by impurities which normally accompany the native molecule when it is produced in vivo. The growth factor of the invention shall be referred to herein as "folliculo stellate-derived endothelial cell growth factor" (FSdGF), since it was originally isolated from bovine folliculo stellate cells, or as "vascular endothelial growth factor" (VEGF). It is to be understood, however, that these terms are intended herein to encompass the protein, regardless of its source or manner of production. For example, the provision herein of FSdGF in isolated form provides the means for isolating cloned DNA sequences encoding the protein, so that it can be produced in commercial quantities using the known techniques of recombinant DNA technology. Furthermore, FSdGF herein is intended to encompass the corresponding proteins produced by other than bovine species, e.g. the human protein, even though it is known that minor variations in amino acid sequence from species to species may occur which do not significantly affect the useful activities of a protein. Using materials and procedures described herein those skilled in the art can obtain, for example, the corresponding human protein by isolating and expressing cloned DNA sequences encoding the protein. Also included within the scope of the term "FSdGF" herein are biologically active fragments thereof, as well as N-terminally and/or C-terminally extended versions thereof, which retain qualitatively the biological activities of the FSdGF described herein. While the form of FSdGF which was isolated using procedures described herein is apparently glycosylated, it is known that production of proteins by recombinant means in certain procaryotic hosts such as *E. coli* generally does not result in glycosylated forms of the protein, but that the resulting unglycosylated forms are often quite useful. Accordingly, the term "FSdGF" encompasses glycosylate and unglycosylated forms of the molecule, provided that they retain qualitatively the biological activities described herein.

FSdGF is a dimeric protein of approximately 43–45 kd, as determined by SDS polyacrylamide gel electrophoresis under non-reducing conditions. It appears to exhibit cell-specific mitagenic activity on vascular endothelial cells. Consequently, FSdGF will find use as a growth factor in a variety of wound healing applications in which it is desired to promote re-endothelialization in the vascular system. FSdGF will be particularly useful as a post-operative would healing agent in both vascular graft surgery and balloon angioplasty. FSdGF can also be employed as a mitogenic agent for growing endothelial cells in vitro. Yet another application for FSdGF is the promotion of vascular wound healing following myocardial infarction.

In accordance with the invention, FSdGF can be obtained in isolated form from conditioned cell culture media containing FSdGF by a process which includes the steps of ammonium sulfate precipitation; heparin sepharose affinity chromatography; exclusion gel chromatography; cation exchange chromatography; and optionally reverse phase high pressure liquid chromatography.

BRIEF DESCRIPTION OF THE FIGURES

FIG. 1A shows the heparin sepharose affinity chromatography (HSAC) of the condition medium by bovine FS cells.

FIG. 1B shows the gel exclusion chromatography of the partially purified HSAC fractions on BioGel P-60.

FIG. 1C shows the chromatographic results on Mono S of the bioactive BioGell P-60 fraction.

FIG. 2A shows the reverse phase HPLC of the Mono S purified and bioactive fractions, and a comparison of the ability of the FS cell conditioned medium at various stages of purification to stimulate the proliferation of low density ACE cells cultures.

FIG. 2B is a comparison of the ability of FS cell conditioned medium at various stages of purification to stimulate the proliferation of low density ACE cell cultures.

FIG. 3 is the NaDodSO$_4$/PAGE of the bioactive fraction purified by RP C$_4$ HPLC.

FIGS. 4A, 4B and 4C are a comparison between the ability of bovine pituitary derived bFGF versus FSdGF to stimulate growth of HUE cells (A), ACE cells (B) and BHK-21 cells (C).

FIG. 5 is a comparison of the ability of bFGF versus FSdGF to stimulate the proliferation of BCE cells, granulosa cells, adrenal cortex cells and BALB/MK cells.

FIG. 6 is a spectrum of reduced/alkylated/lysine blocked FEGF.

FIG. 7 is a trace of the trypsin digestion of the novel growth factor.

FIG. 8 is a graph of the reversed-phase high performance liquid chromatography of bovine follicular cells mitogen activity.

FIGS. 9A and 9B are a NadoSO4/PAGE (12.5 acrylamide) analysis of the most bioactive fraction from the previously shown HPLC profile.

FIG. 10 shows a graph of the proliferation of the low density adrenal cortex derived endothelial cells as a function of time.

FIG. 11 (as 11A, 11B and 11C) shows three photographs of the morphological appearance of low density adrenal cortex endothelial cells.

FIG. 12 is a plot of the heparin-sepharose bioactivity profile of a folliculo cell conditioned medium.

FIG. 13A shows the heparin sepharose affinity chromatography (HSAC) of the condition medium by FS cells.

FIG. 13B shows the gel exclusion chromatography of the partially purified HSAC fractions on Sepharose G/100.

FIG. 13C shows the chromatographic results of Mono S of the bioactive BioGel P-60 fraction.

FIG. 13D shows the reverse phase HPLC of the Mono S purified and bioactive fractions, and a comparison of the ability of the FS cell condition medium at various states of purification to stimulate the proliferation of low density ACE cells cultures.

FIG. 14 is the NaDoDSO$_4$/PAGE of the bioactive fraction purified by RP C$_4$ HPLC.

FIGS. 15A, 15B and 15C are a comparison between the ability of murine derived bFGF versus FSdGF to stimulate growth of HUE cells (A), ACE cells (B) and BHK-21 cells (C).

FIG. 16 is a comparison of the ability of bFGF versus murine growth factor to stimulate the proliferation of BCE cells, granulosa cells, adrenal cortex cells and BALB/MK cells.

FIGS. 13 to 16 refer to the murine source for the growth factor.

DETAILED DESCRIPTION OF THE INVENTION

Definitions

As used herein, the following abbreviations have the indicated meanings:

| | |
|---|---|
| aFGF | acidic fibroblast growth factor |
| bFGF | basic fibroblast growth factor |
| PDGF | platelet derived growth factor |
| TGFα | transforming growth factor α |
| TGFβ | transforming growth factor β |
| EGF | epidermal growth factor |
| PDECGF | platelet derived endothelial cell growth factor |
| FS | folliculo stellate cells |
| FSdGF | folliculo stellate derived growth factor |
| STV | 0.01 M sodium phosphate (pH 7.4), 0.9% NaCl, 0.05% trypsin, 0.02% EDTA |
| CS | calf serum |
| FCS | fetal calf serum |
| PBS | phosphate buffered saline |
| HSAC | heparin sepharose affinity chromatography |
| RP-HPLC | reverse phase high pressure liquid chromatography |
| FPLC | fast high pressure liquid chromatography |
| ACE cells | adrenal cortex-derived capillary endothelial cells |
| HUE cells | human umbilical endothelial cells |
| BCE cells | bovine corneal endothelial cells |
| RIA | radio immunoassay |
| BSA | bovine serum albumin |
| BHK21 | baby hamster kidney-derived fibroblast clone 21 |
| Na Dod SO$_4$ | sodium dodecyl sulfate |
| PAGE | polyacrylamide gel electrophoresis |
| MW | molecular weight |
| kDa | kilo Dalton |
| DMEM | Dublbecco's modified Eagle's medium |

Materials

Bio Gel P-60, Bio Rad protein assay kit, silver nitrate stain kit and low molecular weight standards for Na Dod SO$_4$/PAGE were from Bio Rad (Richmond, Calif.). Heparin Sepharose, Concanavalin A Sepharose, and Mono S column HR5/5 were obtained from Pharmacia (Piscataway, N. J.). The Vydac C$_4$ reverse phase column was purchased from Separation Group (Hesperia, Calif.). Dulbecco's Modified Eagle's Medium (DMEM) was obtained from Grand Island Biological Co. (Grand Island, N. Y.). STV (saline containing 0.05% Trypsin, 0.01 M sodium phosphate pH 7.3 and 0.02% EDTA) was obtained from Difco Lab (Detroit, Mich.). Calf serum (CS) and fetal calf serum (FCS) were obtained by HyClone Sterile Systems, Inc. (Logan, Utah). Tissue culture dishes were purchased from Falcon Plastics (Oxnard, Calif.), except for large scale Nunc culture plates (600 cm$^2$) which were from Applied Scientific (San Francisco, Calif.). Gentamicin was obtained from Schering Co. (Kenilworth, N. J.), and Fungizone was purchased from E. R. Squibb and Sons (Princeton, N. J.). Leupeptin, gelatin, transferring and insulin were Sigma (St. Louis, Mo.). Pituitary derived basic FGF and neutralizing rabbit polyclonal antibodies directed against basic FGF were prepared as previously described (18,19).

Cell Culture

Pituitary derived folliculo stellate (FS) cell cultures were prepared and characterized as previously described (17,20). Confluent cultures, which consisted of homogeneous dome-forming cell monolayers, were dissociated by exposure to STV supplemented with Na$_2$EDTA to a final concentration of 0.3% (4–5 min, 24° C.). The cells were then seeded at a split ratio of 1:10 into large-scale culture plates and grown in the presence of DMEM supplemented with 5% CS, 5% FSC; 50 μg/ml gentamicin and 2.5 μg/ml Fungizone (18). Upon reach confluency, cultures were further passaged or exposed to serum free medium (see below). Cultures of human umbilical endothelial cells (21), bovine brain and adrenal cortex derived capillary endothelial cells (22), bovine granulosa cells (23), adrenal cortex cells (24), corneal endothelial cells (25), baby hamster kidney cells clone 21 (BHK-21)(26), and BALB/MK mouse epidermal keratinocytes (27) (a gift from NIH NCI, Bethesda, Md.) were maintained as previously described (21–27).

Preparation of Condition Medium

Early passage FS cells were plated onto 600 cm$^2$ Nunc plates and grown to confluence over 4 to 5 days in DMEM supplemented with 5% CS, 5% FCS and antibodies as described above. Once domes formation was observed, the monolayers were washed twice with 25 ml of phosphate buffered saline prior to the addition of 150 ml per plate of DMEM supplemented with 50 μg/ml gentamicin, 25 μg/ml Fungizone, 10 μg/ml leupeptin, 5 μg/ml insulin and 10 μg/ml transferrin. After 48 or 72 hr, culture fluids were collected and replaced with the same amount of fresh serum free medium. Collections could be made for a month or more without visible deterioration of the monolayer.

Isolation Procedure

Conditioned medium collected from the confluent monolayers was centrifuged (10,000 g, 15 min) in order to remove floating cells and cell debris. The pH of the supernatant was then adjusted to 5.6 with 6N HCl. Ammonium sulfate (NH$_4$)$_2$SO$_4$ (520 g/liter) was added, and the suspension was set for 6 hr 4° C., the precipitate was then collected by centrifugation (10,000 g, 30 min), redissolved in PBS, and stored at −70° C.

For final isolation, the precipitates from 3 collections (21 liters total of conditioned medium, starting material) were thawed, pooled and then dialyzed overnight at 4° C. against 10 m mM Tris-HCl pH 7.3, 50 mM NaCl. Following dialysis the insoluble material was removed by centrifugation (10,000 g, 30 min) and the supernatant was loaded onto a heparin Sepharose resin (20 ml) that had been equilibrated in 10 mM Tris-HCl pH 7.3, 50 mM NaCl. The resin was washed extensively with the equilibration buffer until the absorbance had returned to baseline, and was then eluted stepwise with increasing NaCl concentrations (0.15 M, 0.45 M, 1 M and 3M NaCl). Aliquots were removed from the fractions for cell proliferation assays, and fractions with the highest bioactivity were pooled and concentrated to 1 ml with an Amicon ultrafiltration cell (Model 12) equipped with a Diaflo YM 10 ultrafiltration membrane.

The concentrated sample was loaded onto a Bio Gel P-60 column (100–200 mesh 1×95 cm) equilibrated at 4° C. in PBS and was eluted with PBS. The Bio Gel P-60 column may be replaced with a Sephadex G-100 which appears to be more efficient. Aliquots of each fraction were taken for cell proliferation assay and the bioactive fractions were pooled, and diluted two fold with 20 mM HEPES pH 8.3. The sample was then applied with a Super loop onto a Mono S column linked to a FPLC system (Pharmacia, Piscataway, N.J.). Elution was achieved with a multilineal gradient (20 mM HEPES pH 8.3 to 20 mM HEPES pH 8.3, 1 M NaCl). After fraction aliquots were tested for bioactivity, the active fractions were pooled and loaded onto a Vydac C$_4$ HPLC column that had been equilibrated in 0.1% trifluoroacetic acid (TFA), 20% acetonitrile. The column was eluted with a linear gradient of 20 to 45% aqueous acetonitrile. Aliquots for the bioassay were then taken, and the column fractions were stored frozen at −70° C.

Cell Proliferation Assays

The mitogenic activity of the column fractions and purified samples was determined by using as target cells adrenal cortex-derived capillary endothelial cells (ACE cells) (22). Stock cultures, maintained in the presence of the DMEM supplemented with 10% CS, 50 μm/ml gentamicin, and 0.25 μm/ml Fungizone were passaged weekly on gelatinized tissue culture dishes at a split ratio of 1:10.

For mitogenic assay, cells were seeded in 12 well cluster plates at a density of 5×10$^3$ cells per well in 1 ml DMEM supplemented with 10% calf serum and antibiotics, as described previously (19). Six hours later, a set of triplicate wells was trypsinized, and cells were counted to determine the plating efficiency. Ten microliter aliquots of the appropriate dilution of each sample, as indicated in the figure legend detailed descriptions below, were then added in triplicate to wells in the dishes on days 0 and 2. After 4 days in culture, the plates were trysin zed, and cell densities were determined with a Coulter counter (Coulter Electronics, Hialeah, Fla.).

The mitogenic activity of the final purified material was also tested on human umbilical endothelial cells, bovine granulosa cells, adrenal cortex cells, corneal endothelial cells, BHK-21 cells and BALB/MK mouse epidermal keratinocytes. For assaying, cells were seeded at an initial density of 2 or 4×10$^4$ cells/35-mm dish. Assays were conducted as described for bovine vascular endothelial cells.

Na Dod SO$_4$/PAGE

Samples were reacted with 250 μCi of Na$^{125}$I using the chloramine T method of iodination (28). After TCA precipitation in the presence of ovalbumin carrier (100 μg/ml), the $^{125}$I-labelled samples (2.5–16×10$^4$ cpm in 10 μl) were analyzed by Na Dod SO$_4$/PAGE, (15% polyacrylamide, ref. 29) under reducing or non reducing conditions. After electrophoresis (5 hr, 20 mAmp) the gels were stained with 0.1% Coomassie blue in 50% trichloroacetic acid for 15 min and destained overnight with 7% acetic acid. Gels were then dried and subjected to autoradiography for 6 to 92 hr.

Protein Microsequencing

For protein sequencing, approximately 5 μg (=200 pmol) of protein from the active fractions of the C$_4$ column were redissolved in 50% trifluoroacetic acid and loaded onto an Applied Biosystems 477A gas-phase protein sequenator. Twelve rounds of Edman degradation were carried out using standard software and chemicals supplied by Applied Biosystems, and identifications of PTH amino acids were made with an automated on-line HPLC column (model 120, Applied Biosystems, Foster City, Calif.).

Growth Factor Isolation and Detection

Preliminary experiments indicated that media conditioned by FS cells contained considerable amounts of mitogenic activity for capillary endothelial cells which could not be neutralized by specific aFGF or bFGF neutralizing polyclonal antibodies. Furthermore when applied to a HS affinity column in 0.6 M NaCl, the majority of the activity was not retained. In contrast, aFGF and bFGF are both retained under similar conditions, and elut from HS at NaCl concentrations of 1.1 M and 1.6 M, respectively (18,30,31). Since cultured pituitary cells are known to produce various growth factors (32), the possibility existed that factors, such as TGFα, EGF and/or TGFβ, might also be present in the conditioned medium from FS cells. ACE cells, which do not respond to TGFα, EGF, or PDGF (22) and for which TGFβ is growth inhibitory (33,34), were therefore used to follow the purification of the novel growth factor.

$(NH_4)_2SO_4$ precipitation provided a convenient way of reducing the volume of the collected conditioned medium from the FS cells to a level suitable for subsequent chromatography. HSAC, which has been used for the purification of other growth factors (32, 33) provided an efficient purification step. Material not retained by the column was inactive and accounted for 50% of the total protein loaded (FIG. 1A). It is likely that the transferrin and insulin components of the cell media were present in the unretained fraction and contributed to the major portion of the proteins. Elution with 0.15 M NaCl yielded a small peak of protein with no bioactivity, while elution with 0.45 M yielded a major peak of protein with 10% of the bioactivity applied to the column. Preliminary experiments had shown that most of the bioactivity could be eluted from HS with 0.6 M NaCl, but that the activity eluted as a broad peak. Therefore, to concentrate the protein peak, elution with 1 M NaCl was carried out. This step gave a relatively narrow protein peak in which 90% of the bioactivity applied on the column was recovered (FIG. 1A). Overall, the HS chromatography resulted in a thirty fold purification, estimated by the protein recovered. Since the growth promoting activity in the starting material was variable, possibly due to the presence of inhibitor, the yield in this step could not be determined exactly (see Table I).

TABLE I

Summary of purification of the Folliculo Stellate derived growth factor

| Purification steps | Protein (μg) | Maximal Stimulation (ng/ml) | $ED_{50}$ (ng/ml) | Total activity (units) | Purification (fold) | Yield % |
|---|---|---|---|---|---|---|
| $(NH_4)_2 SO_4$ ppt | 405000 | 750[a] | 140[a] | $2.9 \times 10^{6a}$ | 1 | —[a] |
| HSAC 1 M NaCl pool[c] | 13464 | 100 | 15 | $9 \times 10^5$ | 30[b] | 100 |
| Bio Gel P-60[c] | 1477 | 10 | 1.5 | $9.8 \times 10^5$ | 300 | 108 |
| Mono S frac 39-42[c] | 244 | 8 | 0.5 | $4.9 \times 10^5$ | 900 | 54 |
| $C_4$ HPLC[d] | 15 | 0.5 | 0.05 | $2.3 \times 10^5$ | 6923 | 25 |

[a]The growth promoting activity in the $(NH_4)_2 SO_4$ was variable, maybe due to the presence of growth inhibitor. Maximal stimulation at saturation was also much lower than that observed for other partially purified (reactions (see FIG. 6). Therefore the yield was based on total activity present in the first partially purified fraction. (HSAC, 1 M NaCl).
[b]The purification in the HSAC step was estimated at 30 fold based on the amount of protein recovered.
[c]Protein was estimated by using the Bradford reagent from Bio Rad with BSA as a standard.
[d]Protein was estimated by AA analysis
[e]The $ED_{50}$ was determined as the protein concentration which gave a half stimulation of cell proliferation in the ACE cell assay. It corresponded to one unit of activity.

HS chromatography was followed by gel exclusion chromatography using Bio Gel P-60 (FIG. 1B). The bioactivity eluted as a major peak with an apparent MW of 40 to 45 kDa. This step resulted in a further ten fold purification with a recovery of 100% (Table I).

The bioactive fractions from the Bio Gel P-60 column were pooled and applied to a Mono S column (FIG. 1C). The bioactive profile of the eluted fractions consisted of two minor peaks of bioactivity eluting respectively of 0.23 M NaCl and 0.28 M NaCl, with a major bioactive peak eluting at 0.33 M NaCl. Analysis of the bioactivity present in the various peaks indicated that the 0.33 M NaCl fractions contained five fold more activity than either the 0.23 M or 0.28 M NaCl peak (data not shown). The Mono S step gave a further three fold increase in specific biological activity over the Bio Gel P-60 step; recovery was about 50% (Table I). The two other bioactive peaks accounted for the remainder of the bioactivity.

Final purification of the endothelial cell mitogenic activity was achieved by RP-HPLC with a $C_4$ Vydac column (FIG. 2A), a preparative method suitable for amino acid sequence analysis. Although losses in biological activity were encountered, presumably because of the acid conditions and solvent used, these were not serious enough to prevent the detection of bioactive fractions. All of the bioactivity detected was present in two closely apposed sharp peaks of protein which, when analyzed by $Na_2$ Dod $SO_4$/PAGE gave the same single band on the silver stained gel (FIG. 3). The RP-HPLC-C4 step resulted in at least a seven fold increase in specific biological activity with a recovery of 50% (Table I). FIG. 2B illustrates the relative potency of the various fractions at different stages of purification.

When the bioactive 0.23 M and 0.28 M NaCl pooled Mono S fractions were chromatographed under similar conditions on the $C_4$ column, a biological profile identical to that observed for the 0.33 M pooled Mono S fractions was obtained. The major portion (90%) of the bioactivity coincided with two closely apposed peaks of proteins which eluted in the same position as those observed with the 0.36 M NaCl Mono S fraction. When analyzed by $Na_2$ Dod $SO_4$/PAGE these peaks gave, under reduced condition, a common band at 23 kDa, migrating in the same position as that observed in FIG. 3.

Physical and Biological Characterization of the Growth Factor

The purified factor when run under unreduced condtions had an estimated molecular weight of 46 kDa (FIG. 3). This value is in good agreement with its elution position on the sizing Bio Gel P-60 column run in solvents expected to maintain the native conformation. When run under reduced conditions the apparent molecular mass was 23 kDa (FIG. 3). From these data, it appears that the mitogen consists of two polypeptide chains with molecular mass of 23 kDa. Given that a single N terminal sequence was obtained, the dimeric molecule is probably composed of two identical or at least very homologous chains.

The apparent indistinctness of the 46 kDa band could be intepreted as indicating the presence of a glycoprotein. In order to explore this point the bioactive HSAC fractions were applied on a concanavalin A Sepharose column in 10 mM Tris pH 7.3, 0.05 M NaCl, 5 mM $MgCl_2$. All of the biological activity was retained by the column. Elution with high salt (0.5 M NaCl) did not elute any significant amount of bioactivity, while elution with 10 mM methylmannoside did result in the recovery of 25% of bioactivity applied on the column. Elution with 0.2 M methylmannoside did not result in further recovery of bioactivity. These results suggest that the factor is a glycoprotein with strong affinity for concanavalin A. However, the poor biological recovery of the factor from that type of affinity chromatography resin makes concanavalin A unsuitable as a step of purification.

The dose response curves for the growth factor depicted in FIGS. 2B and 4 illustrate that as little as about 25 pg/ml stimulates ACE proliferation. Saturation was observed at about 500 pg/ml with an ED 50 of 65 pg/ml (FIG. 4B). These values compared favorably with the range of concentrations where bFGF promotes the proliferation of ACE cells (minimal effect at 10 pg/ml, saturation 200 pg/ml, and ED 50 at 50 pg/ml, ref. 22 and FIG. 4B). However, the final density of the culture grown in presence of the FS derived growth factor was half that of cultures exposed to optimal concentrations of bFGF. Nevertheless, if one considers that the MW of the FS cell derived growth factor is 2.5 times that of bFGF, this new factor has essentially the same potency on a molar basis as bFGF. In addition to its ability to stimulate the proliferation of ACE cells the FS derived growth factor stimulated the growth of bovine brain derived capillary endothelial cells as well as that of HUE cells (FIG. 4A). These results indicate that the mitogenic effect of the factor is not limited by species variation nor by the origin of the vascular endothelial cells. However, and in contrast with bFGF, the factor is not mitogenic for BHK-21 cells (FIG. 4C), nor is it mitogenic for adrenal cortex cells, corneal endothelial cells, granulosa cells or BALB/MK cells (FIG. 5). Therefore, and in contrast with FGF, this factor seems to have a unique specificity for vascular endothelial cells.

Detailed Description of FIGS. 1–7

FIG. 1. Purification of FSdGF by HSAC, Gel Exclusion Chromatography and Mono S Ion Exchange Chromatography A. Approximately 350 ml of the $(NH_4)_2 SO_4$ precipitate fractions derived from 21 liters of FS cell-conditioned medium and dialyzed against 10 mM Tris HCl pH 7.3, 50 mM NaCl, were loaded onto a heparin Sepharose column (1.5 cm×12 cm, 25 ml bed volume) at a flow rate of 150 ml/hr. The column was then washed with 150 ml of the equilibration buffer (20 mM Tris-HCl pH 7.3, 50 mM NaCl), and the retained proteins (50% of the total protein applied on the column) were eluted with a stepwise application of increasing NaCl concentrations (0.15 M, 0.45 M, 1 M and 3 M NaCl.). Fraction size was 2 ml, and the flow rate was 60 ml/hr. Chromatography was performed at 4° C. and absorbancy was monitored at 280 nm. The histogram and open circles show the relative ability of the different pooled or individual fractions to stimulate the proliferation of low density ACE cell clutures (5×10³ cells/35 mm dish). In the case of the pooled fractions (elute, wash and 0.15 M NaCl), aliquots were diluted ten fold in 0.2% gelatin in PBS and 10 µl aliquots were bioassayed. In the case of the individual 0.45 M and 1 M NaCl fractions, aliquots were diluted one hundred fold in 0.2% gelatin in PBS, and 10 µl aliquots were bioassayed. The majority of the biological activity was present in the 1 M NaCl eluate.

B. After concentrating the 1 M NaCl HSAC bioactive fractions 126 to 133 to 1 ml in an Amicon YM10 concentrator, the ultrafiltration retentate was applied on a Bio Gel P-60 column (100–200 mesh, 1×95 cm) equilibrated and run at 4° C. in PBS. The flow rate for development of the column was 6 ml/hr, and 1.45 ml fractions were collected. Absorbancy was monitored at 280 nm. The elution positions of molecular mass markers (in kDa) were as indicated by the arrows. Aliquots of each fraction from the column were diluted 1 to 100 in 0.2% gelatin in PBS, and 10 µl aliquots were bioassayed in ACE cells in 12 well dishes, as described in Material and Methods. Most of the bioactivity eluted as a single peak with an apparent MW of 40 to 45 kDa.

C. The bioactive fractions 26 and 29 eluted from the Bio Gel P-60 column were pooled and diluted three fold with 20 mM HEPES pH 8.3. Using a 50 ml Super loop, the sample was then applied on a Mono S HR 5/5 column equilibrated in the 20 mM HEPES pH 8.3 room temperature. The column was eluted with a multilinear gradient of NaCl (0 M to 1 M) as follows: 0 M NaCl for 5 min, 0 M NaCl to 0.45 M NaCl in 45 min, 0.45 M NaCl to 1 M NaCl in 15 min, 1 M NaCl for 5 min. Absorbancy was monitored at 280 nm. Flow rate was 1 ml per min and 1 ml fractions were collected. Aliquots of each fraction were diluted 1 to 100 in 0.2% gelatin in PBS, and 10 µl aliquots were bioassayed on ACE cells in 12 well dishes as described in Materials and Methods. The histograms show the distribution of the biological activity with most of the biological activity eluting in fractions 37 to 40 (0.33 M NaCl). Fractions indicated by the asterisks were pooled and further examined by RP-HPLC using $C_4$ column.

FIG. 2 Reverse Phase HPLC of the Mono S Purified and Bioactive Fractions and Comparison of the Ability of FS Cell Conditioned Medium at Various Stages of Purification to Stimulate the Proliferation of Low Density ACE Cell Cultures.

A. The active Mono S fractions (fraction 38 to 40; FIG. 3) were loaded onto a Vydac $C_4$ column (25×0.46 cm, 5 µm particle size, 300 A pore size) equilibrated in 0.1% (v/v) TFA, 20% acetonitrile. The arrows shown the times of injection. Protein was eluted with a 115 min linear gradient of 20–45% acetonitrile in 0.1% TFA at a flow rate of 0.6 ml/min, at room temperature. Fractions of 1.5 ml were collected except in the region where the bioactivity was expected to elute; in this region fraction volumes were limited manually to the size of the individual peak fractions. Aliquots of each fraction were diluted 1 to 10 with 0.2% gelatin in PBS and bioassayed as described in material and methods. The histogram shows the distribution of the biological activity. The peak fractions (fractions 25, 26) indicated by the asterisks were used individually for structural studies and further analysis of their biological activity.

B. Low density ACE cell cultures (5×10³ cells/well) were seeded and their proliferation was measured as described in Material and Methods. Samples tested were $(NH_4)_2 SO_4$ precipitate [Δ]; pool of the HSAC 1 M NaCl fractions [▲]; pool of the bioactive Bio Gel P-60 fractions [○]; pool of the bioactive Mono S fractions [□]; bioactive $C_4$ fraction [◇]. Individual points are the mean of triplicate determinations, and standard deviations were less than 10% of the mean. Control cultures exposed to DMEM supplemented with 10% CS had a final cell density of 1.5×10⁴ cell/well.

FIG. 3 NaDodSO$_4$/PAGE of the Bioactive Fractions Purified by $C_4$ RP-HPLC.

The fractions in each of the three peaks of activity from Mono S ion-exchange chromatography step (eluting at 0.23M, 0.28M, and 0.33M NaCl, respectively; see FIG. 1C) were pooled, and each pool was further purified by C4 RP-HPLC, as described in FIG. 2A. In each case, the two peaks of activity eluting from the C4 column (see FIG. 2A) were collected and pooled. Samples of the pooled material from each of the three runs of the C4 column were then subjected to electrophoresis on a 15% polyacrylamide gel, under reducing (lanes 3–5) or non-reducing (lanes 6–8) conditions. The gel was then stained using the silver nitrate stain kit of BioRad. The samples were: lanes 3 and 6, 0.23 M pool; lanes 4 and 7, 0.28M pool; lanes 5 and 8, 0.33M pool. The molecular weight markers runs in lanes 1, 2 and 9 were: bovine serum albumin (MW 66,000), ovalbumin (MW 42,700), carbonic anhydrase (MW 31,000), soybean trypsin inhibitor (MW 21,500), and lysozyme (MW 14,500).

FIG. 4. Comparison of the Ability of Pituitary Derived bFGF Versus FSdGF to Stimulate the Growth of HUE Cells (A), ACE Cells (B), and BHK-21 Cells (C).

(A) Low density cultures of HUE cells ($5 \times 10^3$ cells per 1 cm diameter gelatinized well) were exposed to HEPES (25 mM) buffered medium 199 supplemented with 100 µg.ml heparin, $10^{-8}$M selenium, 20% FCS and increasing concentrations of either pituitary derived bFGF (○) or FSdGF(●). Heparin was added only once at the time of seeding while both bFGF and FSdGF were added every other day. After 6 days in culture, triplicate wells were trypsinized and cell counted. The final desnity of cultures exposed to 20% FCS alone was $1.5 \times 10^4$ cells per well. Standard deviation was less than 10% of the mean.

(B) Low density cultures of ACE cells ($5 \times 10^3$ cells per 1 cm diameter well) were exposed to DMEM supplemented with 10% CS and increasing concentrations of either pituitary derived bFGF (○) or FSdGF(●) added every other day. After 5 days in culture, triplicate wells were trypsinized and cell counted. The final density of cultures exposed to 10% CS alone was $1.3 \times 10^4$ cells per well. Standard deviation was less than 10% of the mean.

(C) Low density cultures of BHK-21 cells ($2 \times 10^4$ cells per 35 mm gelatinized culture dishes) were exposed to 2 ml of DMEM-F12 (1 to 1 v/v) supplemented with 2.5 µg/ml Fungizone, 50 µg/ml gentamicin, 10 µg/ml transferrin, 5 µg/ml insulin and increasing concentrations of either pituitary derived bFGF (○) or FSdGF (●). Insulin and transferrin were added only once, bFGF and FSdGF were added every other day. After 4 days in culture triplicate dishes were trypsinized and cell counted. The final density of culture exposed to transferring and insulin alone was $1.38 \times 10^4$ cells/plate. Standard deviation was less than 10% of the mean.

FIG. 5 Comparison of the Ability of bFGF Versus FSdGF to Stimulate the Proliferation of BCE Cells, Granulosa Cells, Adrenal Cortex Cells and BALB/MK Cells.

$2 \times 10^4$ BCE cells, granulosa cells, or adrenal cortex cells per 35 mm dishes were seeded in the respective media (DMEM supplemented with 10% CS for BCE and adrenal cortex cells and F-12 medium supplemented with 2.5% CS for granulosa cells). BALB/MK cells were seeded at a density of $3 \times 10^4$ cells per 35 mm dishes in low Ca modified Eagle medium (40) supplemented with 10% FCS. Pituitary derived bFGF (bFGF, 2 ng/ml) or FSdGF (5 ng/ml) were added every other day. BALB/MK cells were also exposed to aFGF (10 ng/ml) since this mitogen is as potent as EGF in promoting their growth. After 6 days in cultures, cells were trypsinized and counted in a Coulter counter. Standard deviation was less that 10% of the mean.

Microsequencing Reveals a Unique N-Terminal Amino Acid Sequence

A single amino acid was identified in each of the first 12 cycles, consistent with a homogeneous protein. The yield of the amino terminal residue was 150 picomoles. Unambiguous assignments made for cycles 1 to 12 were as follows: Ala-Pro-Met-Ala-Glu-Gly-Gly-Gln-Lys-Pro-His-Glu. A search of the NBRF database using the FASTP program of Lipman and Pearson (35) found no significant homology between this sequence and any known protein.

Sequence Analysis of Tryptic Peptides

12 µg of FSdGF was reduced in 200 µl of a solution containing 6M guanidine hydrochloride, 0.5M Tris base pH=8, 1 mM EDTA and 10 mM dithiothreitol for one hour at 37° C. The reduced protein was alkylated by the addition of solid iodoacetamide to give a final concentration of 25 mM and the reaction allowed to proceed for 30 minutes at room temperature. Following the alkylation reaction lysines were modified with succinic anhydride. Four aliquots of 5 µl each freshly prepared 100 mg/ml succinic anhydride in acetonitrile were added at five minute intervals. After the final addition the protein was desalted by reverse phase HPLC using a Hewlett-Packard 1090L HPLC equipped with a diode array detector and a 0.46×3 cm Brownlee Labs $C_4$ (BU 300) column. Solvent A was 0.1% TFA in water, solvent B was 0.1% TFA in acetonitrile. The gradient was 20–60% B over 30 minutes at 0.5 ml/min flow rate. The elution profile was monitored at 214 nm and the single protein peak was collected by hand. The chromatogram is shown in FIG. 6. After drying on a Speed-Vac (Savant) the protein redissolved in 200 µl of 100 mM ammonium bicarbonate. 0.4 mg of TPCK treated trypsin was added and the sample was incubated for an additional 2 hours at 37° C. An additional 0.4 µg of trypsin was added after 2 hours and the sample incubated for an additional 2 hours at 37° C. Peptides were separated on the same HPLC using the same solvents as described above. The column was a 0.21×15 cm Vydac $C_{18}$ (218TP5215) run at 0.25 ml/min. The HPLC program initially flowed for 5 minutes at 10% B to and then ran a linear gradient fo 10 to 70% B over 65 minutes. The elution of peptides was monitored at 214 nm and peaks were collected by hand. The chromatogram is shown in FIG. 7. For amino acid sequence analysis peaks 7, 15, 16, 24 and 25 were spotted and dried directly on the glass fiber discs used as supports in the protein sequencer. No sequences were obtained from peptides 15 and 16. Peptide 7 gave a mixed sequence with the major sequence H-Ile-X-Pro-His-Gln-Ser-Gln-His-Ile-Gly-Glu-Met-Ser-Ile-Leu-Gln-His-Asn- and the minor sequence H-X-Val-Leu-Asp/Phe-Val-Val-X-X-Pro-. Peptide 24 gave a single sequence H-Ser-Phe-Cys-Arg-Pro-Ile-Glu-Thr-Leu-Val-Asp-Ile-Phe-Gln-Glu-Tyr-Pro-Asp-Glu-Ile-. Peptide 15 gave a single sequence H-Ser-Phe-Cys-Arg-Pro-Ile-Glu-Thr-Leu-Val-Asp-Ile-Phe-Gln-Glu-Tyr-Pro-Asp-/Ile-Glu. Ser 1 of the peptides 24 and 25 corresponds to Ser 23 of the amino terminal sequence shown above so that these sequences can be merged to give the sequence of the first 42 aminio acids of the protein.

Unambiguous assignments made for cycles 1 to 12 were as follows: Ala-Pro-Met-Ala-Glu-Gly-Gln-Lys-Pro-His-Glu. A search of the NBRF database using the FASTP program of Lipman and Pearson (35) found no significant homology between this sequence and any known protein.

Compositions and Uses

FSdGF provided by the invention is useful as a wound healing agent, particularly in applications where it is desired to re-endothelialize vascular tissue, or where the growth of a new capillary bed (angiogenesis) is important.

FSdGF can, therefore, be used in the treatment of full-thickness wounds such as dermal ulcers, including the categories of pressure sores, venous stasis ulcers and diabetic ulcers. In addition, FSdGF can be used in the treatment of full-thickness burns and injuries site for a skin graft. In this case, the FSdGF is either applied directly to the site or is used to soak the skin that is being transplanted prior to grafting. In a similar fashion, FSdGF will be used in plastic surgery when the reconconstruction is required following a burn, other trauma or for the cosmetic purposes.

Angiogenesis is also important in keeping wounds clean and non-infected. FSdGF can, therefore, be used in association with general surgery and following the repair of cuts and lacerations. It is particularly useful in the treatment of abdominal wounds where leakage of fecal material increases in the risk of infection. Neovascularization is also key to fracture repair since blood vessels develop at the site of bone injury. Adminstration of FSdGF to the site of a fracture is, therefore, another utility.

In the cases where FSdGF is being used for topical wound healing, as described above, it may be administered by any of the routes described below for the reendothelialization of vascular tissue, or more preferably by a topical means. In these cases, it will be administered as either a solution, gel, cream, ointment or as a dry powder directly to the site of injury. Slow release devices direction FSdGF to the injured site will also be used. In topical applications, FSdGF will be applied at concentration ranging from 50 to 1,000 µg/ml either in a single application, or in dosing regimens that are daily or every few days for a period of one to several weeks.

FSdGF can be used as a post-operative wound healing agent in balloon angioplasty, a procedure in which vascular endothelial cells are removed, together with atherosclerotic plaques. FSdGF can be applied to vasuclar endothelial surfaces by systemic or local intravenous application either as intravenous bolus injection or infusions. If desired, the FSdGF can be administered over time using a micrometering pump. Suitable compositions for intravenous administration comprise FSdGF in an amount effective to promote endothelial cell growth and a parenteral carrier material. The FSdGF can be present in the composition over a wide range of concentration, for example, from about 50 g/ml to about 1,000 µg/ml using injections of 3–10 ml per patient. Any of the known parenteral carrier vehicles can be used, such as normal saline or 5–10% dextrose.

FSdGF may also be used to promote endothelialization in vascular graft surgery. In the case of either vascular grafts using transplanted vessels of synthetic material, for example, FSdGF can be applied to the surfaces of the graft and/or at the junctions of the graft and the existing vasculature in order to promote the growth of vascular endothelial cells. For such applications, the FSdGF may be applied intravenously as described above for balloon angioplasty or it may be applied directly to the surfaces of the graft and/or the existing vasculature either before or during surgery. In such cases, it may be desired to apply the FSdGF in a thickened carrier material so that it will adhere to the affected surface. Suitable carrier materials include, for example, 1–5% carbopol. The FSdGF may be present in the carrier over a wide range of concentrations, for example, from about 50 µg/mg to about 1000 µg/mg.

FSdGF may also be employed to repair vascular damage following myocardial infarction. The FSdGF is administered intravenously for this purpose, either in individual injections or by micrometering pump over a period of time as described above.

FSdGF may also be used as a growth factor for the in vitro culturing of endothelial cells. For such uses, FSdGF can be added to the cell culture medium at a concentration from about 10 ng/ml to about 10 µg/ml.

The amino acid sequence of FSdGF will be used to design synthetic oligonucleotide probes for the retrieval of the FSdGF gene. These probes will either be of a mixed sequence based on all possible genetic code choices, or will be of single sequence based on codon choice preferences and other factors. In the first instances, probes based on the amino acid sequence of bovine FSdGF will be used to screen either bovine cDNA libraries made from folliculostellate cells, or bovine genomic libraries. Bovine DNA clones encoding FSdGF thus isolated will be sequenced to determine the complete coding and hence amino acid sequence of bovine FSdGF. The bovine FSdGF clones will then be used as probes to isolate human FSdGF sequences from either cDNA libraries generated from tissues shown to express the factor, or from human genomic libraries. In this way, the complete nucleotide and hence amino acid sequence of human FSdGF can be established.

Discussion

This is the first identification, purification and biological characterization of a novel heparin-binding endothelial cell growth factor (VEGF) from culture media conditioned by pituitary FC. Additional detail is provided in the Examples below.

Results

The media conditioned by FC was found to stimulate the proliferation rate of low-density microvascular endothelial cells. Table 2 summarizes the steps for the purification of the growth promoting activity and the corresponding yield in bioactivity. The mitogenic activity was precipitated by 50% ammonium sulfate and resuspended to a volume suitable for subsequent purification. The H-S step provided an efficient way of further concentrating such activity and also provided a ten fold purification. Approximately 90% of the biological activity was eluted in the presence of 0.9 M NaCl (FIG. 8). The bioactivity was not affected heating the fractions at 65° C. for 5 min and was decreased 25–30% following the exposure to 0.1% TFA (pH 2) for two hours.

TABLE 2

Summary of purification of VEGF from 6 liters of conditioned medium.

| Purification step | Protein (ug) | Maximal stimulation (ng/ml) | Purification (fold) | Yield (%) |
|---|---|---|---|---|
| C.M.⁺ | 190.000 | 2500 | 1 | 100 |
| A.S.⁺ | 175.000 | 2500 | 1 | 92 |
| H-S⁺ | 13.000 | 250 | 10 | 68 |
| R-P 1^ | 25 | 5 | 500 | 6 |
| R-P 2^ | 4 | 1.2 | 2000 | 4 |

C.M. conditioned medium:
A.S. ammonium sulfate precipitate:
H-S. heparin-sepharose:
R-P 1, reversed phase HPLC step 1:
R-P 2, reversed phase HPLC step 2.
⁺protein concentration was determined by Bio Rad Kit
^protein concentration was determined by comparing the relative intensities of bands with standards in silver-stained SDS/PAGE.

The most bioactive H-S fractions was applied to a semi preparative C4 reversed phase HPLC column, a method suitable for rapid purification of proteins and peptides. The bioactivity was eluted as a single peak in the presence of about 29% acetonitrile (FIG. 9A). A silver-stained (56) SDS/PAGE gel on the most bioactive fractions revealed the presence of three or four bands. These fractions were further purified by a second reversed phase HPLC step, using an analytical C4 column which was eluted with a gradient of 2-propanol, instead of acetonitrile. A single peak of bioactivity corresponding to a distinct peak in the absorption profile was obtained. (FIG. 9B).

The peak fractions from the second reversed phase step displayed a single band on a silver stained SDS/PAGE, with an apparent $M_r$ of about 23 kDa under reducing conditions (FIG. 10). The intensity of staining of the band was highly correlated to the mitogenic activity across the bioactivity profile. Because previous experiments, using a molecular sieve with a TSK G 3000 SW column, suggested a $M_r$ in the range of 40–43 kDa, the possibility that the growth factor in native conditions is a dimer was considered. This was strongly suggested by the finding that the purified material had an apparent $M_r$ Of about 45 kDa in a silver stained SDS-PAGE under non-reducing conditions (see FIG. 10).

As illustrated in FIG. 11, the dose response curve for the purified growth factor revealed a half maximal effect on adrenal cortex-derived capillary endothelial cells proliferation at 150–200 pg/ml and a maximal effect at 1–1.5 ng/ml. These values were derived from protein sequencing and were found to be in good agreement with those obtained by comparing the relative intensitieis of bands with standards in silver stained SDS/PAGE.

Gas phase microsequencing of the purified material demonstrated unambiguously a single N-terminal amino acid sequence. The first five residues are Ala-Pro-Met-Ala-Glu. Another way to describe the N-terminal amino acid sequence is Ala-Pro-Met-Ala-Glu-Gly-Gly-Gln-Lys-Pro-His-Glu-Val-Val-Lys-Phe-Met-Asp-Val-Tyr-Gln-(Arg)-Ser-Phe-X-Arg-Pro-Ile-Glu-Thr-Leu-(Val)-X-Ile-X-(Gln)-Glu-Tyr-(Pro)- where the amino acids in parenthesis are known with a high degree of certainty and —X— denotes an amino acid of as yet unknown identity. A computer search revealed that such a sequence does not display significant homology to any previously known protein.

The bioactivity of the growth factor was also tested with different cell types. As shown in FIG. 12, appreciable activity was observed only in cell types of vascular endothelial origin, such as fetal and adult bovine aortic endothelial cells, bovine brain capillary endothelial cells and human umbilical vein endothelial cells. In contrast, adrenal cortex cells, lens epithelial cells, corneal endothelial cells, BHK-21 fibroblasts and keratinocytes failed to show any significant mitogenic response.

The growth factor was purified by using a combination of ammonium sulfate precipitation, H-S affinity chromatograph and two reversed phase HPLC steps. Analysis of the purified material by SDS PAGE reveale a $M_r$ of about 45 kDa under non reducing conditions. When the material was analyzed in the presence of 2-mercaptoethanol, a single band with a $M_r$ of 23 kDa was visualized, indicating that the growth factor is a dimer composed of two subunits of identical apparent molecular weight. Microsequencing of the purified material reveals a unique N-terminal amino acid sequence.

The growth factor was heat and acid stable and its p.I., as estimated by chromatofocusing on a Mono P column is about 8.5.

The purified growth factor was able to stimulate the proliferation of vascular endothelial cells at concentrations between 25 pg and 1–1.5 ng/ml. These values, assuming a $M_r$ of 45 kDa, correspond respectively to 0.55 pM and 22–33 pM. Such values are in the same range as those obtained with bFGF (2,56). However, the novel growth factor did not induce any appreciable mitogenic effect on corneal endothelial cells, lens epithelial cells, BHK-21 fibroblasts, adrenal cortex cells, or keratynocytes. In contrast, bFGF and aFGF are both potent mitogens for all of these cell types (2,56).

The ability of VEGF to bind heparin may have implications as to its in vivo function and regulation. Heparin sulphates are fundamental components of the extracellular matrix and have been proposed to play a crucial role in determining contact between target cells and heparin-binding growth factors (16,57,58,59).

The presence of VEGF in pituitary FC indicates a role for these cells in the development, organization and maintenance of a differentiated state of the complex microvasculature of the adenohypophysis.

It is presently unknown whether VEGF is expressed in organs other than the pituitary gland. However, considering the fundamental role of vascular endothelial cells growth and angiogenesis in a great variety of normal and pathological proliferations (60), it is expected that the distribution of the growth factor is widespread. With this context, it is of interest that PDGF, EGF, TGF alfa, TGF beta, FGF, NGF, which were initially believed to be restricted to specific cells or tissues, were later found to have a much broader and sometimes ubiquitous distribution (61).

The genes for bFGF and aFGF, the best characterized endothelial cell mitogens, do not code for a conventional signal peptide (17, 43). Accordingly, these growth factors appear to be sequestered inside the cells of origin and apparently do not have direct access to target cells (2, 15,45). It has been suggested that bFGF may be incorporated into the basement membrane and be subsequently released in a soluble form only when the matrix is degraded following the action of specific enzymes (16). Such a mechanism of release suggests a role for the growth factor mostly or exclusively in events which involve degradation of the basement membrane or cell lysis, such as organ remodeling, wound healing or neoplasia (60).

In contrast, a soluble endothelial cell growth factor such as VEGF may play a more dynamic role in the physiological regulation of the vascular endothelial cells proliferation, either in the cyclical growth of blood vessels which takes place in organs such as the corpus luteum (62) or in the tonic maintenace of the differentiated stage of the endothelium in the vascular tree.

Unlike bFGF or aFGF, which are active on a very broad spectrum of cells (2,56), VEGF appears to be specific for vascular endothelial cells. VEGF is special therapeutic significance for conditions in which a selective action on the vascular endothelial cells, in the absence of excessive connective tissue proliferation, is desirable, such as diabetic ulcers or traumatic vascular injuries.

Detailed Description of FIGS. 8 to 12

FIG. 8—Heparin-sepharose (H-S) bioactivity profile of FC conditioned medium. The medium (6 liters) was concentrated and applied to a H-S which had been preequilibrated in 10 mM Tris/Cl, pH 7.2 containing 50 mM NaCl. The column was washed with the same buffer and then eluted sequentially with 10 mM Tris/Cl, pH 7.2, containing 0.15, 0.9 nd 3 M NaCl. Aliquots of the collected fractions were diluted 100 fold in 0.2% gelatin in PBS 5 μl/ml were applied to capillary endothelial cells for bioassay.

FIGS. 9A and 9B-Sequential reversed phase HPLC profiles of endothelial cell mitogenic activity. The most bioactive H-S fractions were applied to a C4 column (10×250 mm) preequilibrated with 0.1% TFA/20% acetontrile (panel A). After the column was washed with 10 ml of equilibration buffer, the sample was eluted with a linear gradient of acetonitrile. Aliquots of each fraction were diluted tenfold with 0.2% gelatin in PBS and 5 μl/ml were applied to capillary endothelial cells for bioassay. The most bioactive fractions were pooled and applied to a C4 column (4.6×250 mm) which had been preequilibrated with 0.1% TFA/20% 2-propanol (panel B). After washing the column with 3 ml of equilibration buffer, the sample was eluted with a linear gradient of 2-propanol. Aliquots of fractions were tested for bioactivity.

FIG. 10—NaDodSO$_4$/PAGE analysis of most bioactive fraction from chromatogram shown in FIG. 9B. Two 50 μl aliquots of such fraction were dried in a speed vac and redissolved in sample buffer containing (+) or not (−) 2.5% 2-mercaptoethanol. The samples were heat-denatured and electrophoresed in a 12.5% PAGE which was subsequently silver stained. The molecular weight markers are: phosphorylase B, 97,400; bovine serum albumin, 66,200; ovalbumin, 43,000; carbonic anhydrase, 31,000; soybean trypsin inhibitor, 21,500; lysozyme, 14,400.

FIG. 11—Dose-responsive growth of adrenal cortex derived capillary endothelial in the presence of purified VEGF. Cells were seeded at the density of $1 \times 10^4$/well in 12 well plates. The indicated amounts of VEGF were added a few hours after plating in 5 µl/ml aliquots. After five days, cells were counted in a Coulter counter. The results shown represent mean values of three separate experiments conducted in duplicate. Duplicates in each experiment varied less than 10%.

FIG. 12—Effects of VEGF on the growth of different cell types. CEC, corneal endothelial cells; BAC, bovine adrenal cortex cells; KTC, keratynocytes; LEC, lens epithelial cells; BHK-21, baby hamster kidney cells, clone 21; ACC, adrenal cortex capillary endothelial cells; BBC, bovine brain capillary endothelial cells; HUVE, human umbilical vein endothelial cells; FBAE, fetal bovine aortic endothelial cells, ABAE, adult bovine aortic endothelial cell. Cells were seeded in their respective growth media, incubated with a maximal concentration of VEGF and counted after 4 or 5 days. Results are expressed as a percent of appropriate control.

Angiogenesis is a multi-step phenomenon which involves capillary endothelial cell profileration, migration and tissue infiltration[1]. It plays a central role in a variety of physiological and pathological process such as embryonic development, wound healing, atherosclerosis and tumor growth[1,2]. Several factors that induce angiogenesis have recently been isolated and characterized. Of these, only the basic and acidic forms of FGF have been shown to directly control all steps of angiogenesis including vascular endothelial cell proliferation, migration and increased expression of plasminogen activator and collagenase activity[2].

Despite the evidence the FGF is angiogenic, two puzzling questions point to the existence of other angiogenic factors which could complement the action of FGF. First, FGF lacks the hydrophobic signal sequences that govern secretion[12,13], yet for acceptance as an angiogenic factor any putative mediator should be shown to be a diffusible substance which induces new capillary formation from a microcirculatory bed. Second, FGF is produced by endothelial cells themselves[14,15]. If FGF is present in and around endothelial cells yet the cells are quiescent, other factors must come into play to trigger angiogenesis.

The present invention also relates to the isolation and characterization of a new endothelial cell mitogen produced and secreted by AtT-20 cells. This mouse cell line is available from The America Type Culture Collection, 12301 Parklawn Drive, Rockville, Md. The factor producedby AtT-20 cells has a unique target cell specificity, since it stimulates only vascular endothelial cells to proliferate and does not affect other cell types sensitive to FGF.

This factor was discovered during studies on expression of bFGF and possible secretory pathways the pituitary cell line AtT-20[5]. The cells were transfected with a chimaeric bFGF gene composed of the coding sequence for the growth hormone secretion signal peptide fused with the coding sequence for the bFGG gene[6]. The murine cell line was selected because it has retained normal secretory functions and can be used to study the molecular events involved in packaging and secretion of protein[5]. It was hoped that the bFGF expressed would have been secreted by these cells either through a constitutive secretory pathway or through a secretory pathway involving secretory granules. When medium conditioned by transfected AtT-20 cells were examined for angiogenic activity, a considerable amount of activity was present which could not be immunoneutralized by antibodies against bFGF and which did not crossreact in a (RIA) specific for bFGF. Likewise, media conditioned by parental cells which did not express the bFGF gene also contained a considerable amount of bioactivity, suggested that a factor unrelated to bFGF was responsible for it.

The endothelial cell mitogen present in the conditioned medium was then purified by a combination of steps including heparin sepharose affinity chromatography (HSAC), exclusion gel chromatography on Sephadex G 100, cation exchange on chromatography on Mono S resin, and finally, by PR-HPLC with a C4 Vydac column (see Table 3). Fractions were assayed for bioactivity using adrenal cortex derived capillary endothelial cells. When the collected material was applied on HS under the conditions described in FIG. 13A the activity eluted in a broad peak in the range of 0.5 to 0.6M. In order to concentrate it, elution with 0.8 M NaCl was carried. This material when applied on Sephadex G 100 gave a major peak of bioactivity which eluted with an apparent MW of about 45 kDa (FIG. 13B). When chromatographed on Mono S under the conditions indicated FIG. 13C, a single, major, bioactive peak was observed eluting at 0.28 M NaCl. Final purification was achieved by RP-HPLC using a C4 Vydac column (FIG. 13D). All of the bioactivity detected was present in 2 closely sharp peaks of proteins which when analyzed by $Na_2DodSO4$/PAGE under non reducing conditions gave a single band with an apparent molecular weight of 45 kDa. When seen under reducing conditions, the band had an apparent molecular weight of 23 kDa (FIG. 13D). In one of the fractions, a small amount of contaminant with a MW of 27 kDa whose migration was not affected by reduction was also present. This contaminant did not amount to more than 5% of the total. When the major peak activity was rerun under identical condition of a C4 column, a single peak of protein with a small shoulder

TABLE 3

Summary of purification of the AtT-20 derived growth factor

| Purification steps | Protein (µg)[a] | $ED_{50}$[b] (mg/ml) | Total activity | Yield (%) | Purification (Fold) |
|---|---|---|---|---|---|
| (NH4) SO4 | 480,000 | 1500 | 320,000 | 100 | 1 |
| HSAC | 180,000 | 36 | 522,000 | 163 | 42 |
| G100 | 1,500 | 7 | 210,000 | 65 | 214 |
| Mono S | 72 | 0.4 | 180,000 | 56 | 3,750 |
| RP HPLC C4 | 7[c] | 0.15 | 43,000 | 13 | 10,000 |

[a]Protein was estimated by using the Bradford reagent from Bio Rad with BSA as a standard.
[b]The $ED_{50}$ was determined as the protein concentration which gave a half stimulation of cell proliferation in the ACE cell assay. It corresponds to one unit of activity.
[c]Protein was determined by using $E_{210}^{1\%} = 140$.

was obtained (FIG. 13D). Microsequencing of this material reveals a unique terminal amino acid sequence. Approximately 2 µg (80 pmole) of protein was sequenced using an Applied Biosystems 477A gas phase protein sequenator. A single amino acid was identified in each of the first 24 cycles consistent with a homogeneous protein. The yield of the amino terminal residue was 30 pmole. Unambiguous assignment modes for cycles 1 to 5 were as follows: Ala-Pro-Met-Ala-Glu. A longer amino acid sequence for the growth factor from AtT-20 was later determined and is described below.

A search of the NBRF database using the FASTP program of Lipman and Pearson[35] found no significant homology between the sequence of the first 22 amino acids and any known protein.

The dose response curve for the growth factor depicted in FIG. 15B illustrates that as little as 50 pg/ml stimulates ACE proliferation. Saturation was observed at 1 ng/ml with an ED$_{50}$ of 150 pg/ml. These values compared favorably with the range of concentrations where bFGF promotes the proliferation of ACE cells (minimal effect at about 10 pg/ml saturation at about 200 pg/ml and ED$_{50}$ at 50 pg/ml,[22] and FIG. 15). However, the final density of the culture grown in presence of the AtT-20 derived growth factor was half that of cultures exposed to optimal concentrations of bFGF, indicating that the average doubling time of the ACE cells was longer when driven to proliferate by the AtT-20 derived growth factor than by bFGF. Nevertheless, if one considers that the MW of the AtT-20 cell derived growth factor is 2.5 times that of bFGF it would indicate that it has about the same potency as bFGF. In addition to its ability to stimulate the proliferation of ACE cells the AtTC-20 derived growth factor did stimulate the growth of bovine brain derived capillary endothelial cells as well as that of HUE cells (FIG. 15A). This indicates that its mitogenic effect was not limited by species variation nor by the origin of the vascular endothelial cells. Surprisingly, it did not stimulate the proliferation of even BHK-21 cells, a cell line known to respond to a wide variety of mitogens including TGFα, EGF PDGF, TGFβ and aFGF or bFGF (as reviewed in [26]), nor was it mitogenic for adrenal cortex cells, corneal endothelial cells, granulosa cells, vascular smooth muscle cells or BALB/MK cells (FIG. 15D). Therefore, and in contrast with FGF, it seems to have a unique specificity for vascular endothelial cells. The present data established that AtT-20 cells which have retained many important chemical and physiological properties of pituitary corticotroph, in particular the ability to synthesize and release as major secretory products ACTH, B-lipotropin and B-endorphin[64], do also produce an angiogenic factor.

The physical properties of growth factor (MW 45 kDa, basic pI, affinity for HS) and biological properties (mitogenic for vascular endothelial cells) indicate that it is distinct from other known growth factors such as EGF, TGFα, PDGF, TGFB or the recently reported keratinocyte growth factor[21]. Its lack of recognition by neutralizing polyclonal antibodies directed against aFGF or bFGF as well as its lack of cross reactivity in RIA specific for aFGF or bFGF indicates that it is distinct from FGF. It seems also to be distinct from the recently reported platelet derived endothelial cell growth factor[37] have the same apparent target cell specificity and similar molecular mass, they differ by twenty fold in potency and by their secondary structure, PDECGF being a single chain polypeptide while the AtT-20 growth factor has a dimeric structure.

The unique target cell specificity and N-terminal lead to the conclusion that the AtT-20 derived growth factor represents a previously unknown growth factor. Although the present study clearly established that this novel growth facto is mitogenic for capillary endothelial cells, it is not yet known whether it can stimulate other events linked to angiogenesis. These include chemotaxis of capillary endothelial cells and activation of the synthesis of cellular enzymes such as collagenase and plasminogen activator which are involved in the breakdown of capillary basement membrane[3]. In view of its preferential activity on vascular endothelial cells as compared to other mesoderm derived cells, the name of vasculotropin is suggested for this novel growth factor.

Available structural data should allow studies on the cloning, structure, topology, expression and regulation of the growth factor gene in both physiological and pathological conditions. These studies may provide clues as to its distribution in normal versus malignant tissues as well as to its physiological functions including angiogenesis.

Detailed Description of FIGS. 13–16

FIG. 13 Purification at AtT20 Growth Factor by HSAC, Gel Exclusion Chromatography, Mono S Ion Exchange Chromatography, and R-HPLC on C$_4$ Column 13A. Approximately 490 ml of the (NH$_4$)$_2$SO$_4$ precipitate fractions derived from 30 liters (6 collection of 5 liters at 2 day intervals) of AtT-20 cell-conditioned medium (DMEM-H21) supplemented with 5 μg/ml insulin and 10 μg/ml transferrin) and dialyzed against 10 mM Tris HCl pH 7.3, mM NaCl, were loaded onto a heparin Sepharose column (1.5 cm×12 cm, 25 ml bed volume) at a flow rate of 150 ml/hr. The column was then washed with 150 ml of the equilibration buffer (20 mM Tris-HCl pH 7.3, 50 mM NaCl), and the retained proteins (50% of the total protein applied on the column) were eluted with a stepwise application of increasing NaCl concentrations (0.3 M, 0.8 M and 3 M NaCl). Fraction size was 3 ml, and the flow rate was 6 ml/hr. Chromatography was performed at 4° C. and absorbency was monitored at 280 nm. The histogram and closed circles shown the relative ability of the different pooled or individual fractions to stimulate the proliferation of low density ACE cell cultures (5×1 cells/well, 12 well dishes). Conditions for testing were the same as those described in [37]. The majority of the biological activity was present in the 0.8 M NaCl eluate.

13B. After concentrating the 0.8 M NaCl HSAC bioactive fractions to 1 ml in Amicon YM10 concentrator, the ultrafiltration retentate was applied on a Sephadex G 100 column (1×95 cm) equilibrate and run at 4° C. in PBS. The flow rate for development of the column (1×95 cm) equilibrated and run at 4° C. in PBS. The flow rate for development of the column was 6 ml/hr, and 3 ml fractions were collected. Absorbency was monitored at 280 nm. The elution positions of molecular mass markers (in kDa) were as indicated by the arrows. Aliquots of each fraction from the column were diluted 1 to 100 in 0.2% gelatin in PBS, and 10 μl aliquots were bioassayed.

13C. The bioactive fractions eluted from the Sephadex G 100 column were pooled and diluted three fold with 20 mM HEPES pH 8.3. Using a 50 ml Super loop, the sample was then applied on a Mono S HR 5/5 column equilibrated in the 20 mM Hepes pH 8.3 at room temperature. The column was eluted with a multilinear gradient of NaCl (0 M to 1 M) as follows: 0 M NaCl for 5 min., 0 M NaCl to 0.45 M NaCl in 45 min, 0.45 M NaCl to 1 M NaCl in 15 min, 1 M NaCl for 5 min. Absorbency was monitored at 280 nm. Flow rate was 1 ml per min and 1 ml fractions were collected. Aliquots of each fraction were diluted 1 to 100 in 0.2% gelatin in PBS, and 10 μl aliquots were bioassyed on ACE cells in 12 well dishes as described above. The histogram shows the distribution of biological activity with most of the biological activity eluting in fractions 33 to 35 (0.28 M NaCl).

13D. The active Mono S fractions (fraction 33 to 35; FIG. 3 were loaded onto a Vydac C$_4$ column (25×0.46 cm, 5 μm particle size, 300 A pore size) equilibrated in 0.1% (v/v) TFA, 20% acetonitrile. The arrows show the times of injection. Protein was eluted with a 115 min linear gradient of 20–45% acetonitrile in 0.1% TFA at a flow rate of 0.6 ml/min, at room temperature. Fractions of 1.5 ml were collected. Aliquots of each fraction were diluted 1 to 10 with 0.2% gelatin in PBS and bioassayed as described above. The histogram shows the distribution of the biological activity. The peak fractions [22, 24] were used individually for structural studies and further analysis of their biological activity. (a) The major peak of activity was rerun on the same columns as shown in insert b, the peak fractions were taken for amino and terminal sequence analysis. (b) $^{125}$I labelled protein samples of the fraction 22 (lane A,C) and 23 (lane B,D) were analyzed individually under unreduced (lane A,B) or reduced conditions (lane C,D).

FIG. 14—Electrophoresis was performed under the conditions described herein. Non-reduced conditions showed a component at about 43–45 kDa. The reduced conditions showed a component at about 23 kDa. After electrophoresis the gels were stained with Coomassie blue, destained, dried and subjected to autoradiography. Migration of the samples was compared to that unreduced (left) or reduced (right) protein standards: 97, 66, 43, 30, 21 kDa.

FIG. 15 Comparison of the ability of pituitary derived bFGF versus the AtT-20 cell derived growth factor to stimulate the growth of HUE cells (A), ACE cells (B), and BHK-21 cells (C).

15A. Low density cultures of HUE cells[21] ($5 \times 10^3$ cells per 1 cm diameter gelatinized well) were exposed to HEPES (25 mM) buffered medium 199 supplemented with 100 µg/ml heparin, $10^{-8}$M selenium, 20% FSC (as described in [11]) and increasing concentration of either pituitary derived bFGF (O) or AtT-20 cells derived growth factor (●). Heparin was added only once at the time of seeding while both bFGF and AtT-20 cells derived growth factor were added every other day. After 6 days in culture, triplicate wells were trypsinized and cell counted. The final density of cultures exposed to 20% FCS alone was $7.4 \times 10^4$ cells per well. Standard deviation was less than 10% of the mean.

15B. Low density cultures of ACE cells ($5 \times 10^3$ cells per 1 cm diameter well) were exposed to DMEM supplemented with 10% CS and increasing concentrations of either pituitary derived bFGF (●) or the AtT-20 cell derived growth factor (O) added every other day. After 5 days in cultures, triplicate wells were trysinized and cell counted. The final density of culture exposed to 10% CS alone was $1.3 \times 10^4$ cells per well. Standard deviation was less than 10% of the mean.

15C. Low density of BHK-21 cells[26] ($2 \times 10^4$ cells per 35 mm gelatinized tissue culture dishes) were exposed to 2 ml of DMEM-F12 (1 to 1 v/v) supplemented with 1.5 µg/ml gentamicin, 10 µg/ml transferring, 5 µg/ml insulin and increasing concentrations of either pituitary derived bFGF (●) or the AtT-20 cells derived growth factor (O). Insulin and transferrin were added only once, bFGF and AtT-20 cells derived growth facto were added every other day. After 4 days in culture triplicate dishes were trypsinized and cell counted. The final density of culture exposed to transferrin insulin alone was $1.05 \times 10^4$ cells/plate. Standard deviation was less than 10% of the mean.

16. BALB/MK cells[14] were seeded at a density of $3 \times 10^4$ cells per 35 mm dishes in low Ca modified Eagle medium [15] supplemented with 10% FCS. $2 \times 10^4$ BCE cells[16] granulosa cells[17], or adrenal cortex cells[18] per 35 mm dishes were seeded in their respective media (DMEM supplemented with 10% FCS, 5% CS, 10% CS for BCE and adrenal cortex cells and F-12 medium supplemented with 2.5% CS for granulosa cells). Pituitary derived bFGF (bFGF, 2 ng/ml) or AtT-20 cell derived growth factor (1.5 ng/ml) were added every other day. BALB/MK cells were also exposed to aFGF (10 ng/ml) since this mitogen is as potent as EGF in promoting their growth. After 6 days in cultures, cells were trypsinized and counted in a Coulter counter. Standard deviation was less than 10% of the mean.

An advantage of culturing the bovine cells to collect the growth factor is that the overall cell structure has good cohesive integrity. That is to say, the cell layer usually remains intact for collecting the conditioning medium for many days, and even over a month or more of successive collection of the media samples. When the dome structure is present, it is possible to collect samples from above the dome and also from within or below the dome. Normally, the growth factor is in a higher concentration within the dome.

A disadvantage observed during the culturing of the bovine cells is that these cells produce a large amount of different proteins, which are secreted from the cell. Thus the purification steps need to be able to remove more of the undesired protein.

An advantage of the AtT-20 cell line is that it is commercially available.

An advantage of the culturing of the murine cells, AtT-20, is that these cells produce the novel growth factor without producing a large amount of other proteins which might interfere with the subsequent isolation steps.

A disadvantage of culturing the murine cells AtT-20 is that the structural integrity of the cell culture layer is not high. Thus during the culturing and collection, small portions of the cell layer will break away, float in the conditioning media and then die. Often the culturing of the murine cells is only possible up to about 7 days or slightly longer.

The novel growth factor from bovine sources is often of sufficient purity after the mono S step and a Sephadex G-100 step that the RP HPCL-C4 purification is not necessary. RP HPLC can be sued to determine the purity of the FsdGF.

Murine Growth Factor Amino Acid Sequence

The N-terminal sequence was determined for the growth factor protein derived from mouse AtT20 cells. Two N-terminal sequencing runs were carried out on the protein in an Applied Biosystems gas-phase protein sequencer. The second run, the sequencer was loaded with approximately 2.5 times as much of the protein as the first run.

As a result of comparing the data, from the two sequencing runs, the following N-termianl sequence was determined:

X'-Pro-Thr-Thr-Glu-Gly-Glu-Gln-Lys-Ala His-Glu-Val-Val-Lys-Phe-Met-Asp-Val-Tyr-Gln-Arg-Ser- . . .

At amino acid position one (X')-three different amino acids were detected (Ala, Gly and Ser), with Ala being the most prominent. Since this amino acid residue was ambiguous, the residue is represented by a "X".

Comparison of the sequence from the mouse AtT20 cells with the N-terminal 23 amino acids determined for the bovine FSdGF protein demonstates that these two proteins are substantially homologous:

mouse
AtT20 prot.: X'-Pro-Thr-Thr-Glu-Gly-Glu-Gln-Lys-Ala His-Glu-Val-Val-Lys-Phe-Met-Asp-Val-Tyr-Gln-Arg-Ser- . . .

bovine
FSdGF: Ala-Pro-Met-Ala-Glu-Gly-Gly-Gln-Lys-Pro-His-Glu-Val-Val-Lys-Phe-Met-Asp-Val-Tyr-Gln-Arg-Ser- . . .

The following Examples are provided to be illustrative and exemplary only. They are not to be construed as being limiting in any way.

Reagents—Tissue culture media and reagents were obtained from Gibco (Grand Island, N.Y.). Acetonitrile and 2-propanol were purchased from Fisher Sci. (Fair Lawn, N.J.). Heparin-sepharose (H-S) was obtained from Pharmacia (Piscataway, N.J.). Vydac HPLC columns were from The Separation Group (Hesperia, Calif.). Molecular weight markers for PAGE and protein determination kit were from Bio Rad Labs (Richmond, Calif.). Tissue culture plates were purchased from Costar, except for large scale Nunc plates (24.5×24.5 cm), which were Applied Sci. (San Francisco, Calif.). All other reagents were from Sigma Chemical Co. (St. Louis, Mo.) or Applied Biosystems (Foster City, Calif.).

EXAMPLE A

Purpose of this Example was the determination of the molecular weight of the endothelial cell growth factor secreted in the medium by follicular cells.

Confluent cultures of follicular cells were incubated for three days in a serum-free medium consisting of low glucose Dulbecco's modified Eagle's medium supplemented with transferrin (10 μl/ml), insulin (5 μg/ml), 2 mM glutamine and antibiotics. The conditioned medium (CM) (150 ml) was then collected centrifuged (10000×g, 15 min. 4° C.) in order to remove cell debris, and then applied to a Heparin-Sepharose column which had been preequilibrated with 10 mM Tris/Cl, pH 7.0. The column was then sequentially eluted with 10 mM Tris/Cl, pH 7.0 containing 0.6, 1 and 3 M NaCl. The flow rate was 21 ml/h. Fractions of 700 μl were collected and aliquots were tested for bioactivity on adrenal cortex-derived microvascular endothelial cells. The majority of the bioactivity was eluted in the present of 0.6 M NaCl. This chromatographic behavior is different from that of aFGF or bFGF, which are known to elute, respectively, in the presence of 0.9–1.1 M NaCl and 1.8–2.2 M NaCl.

The most bioactive 0.6 NaCl fractions were pooled and further examined for determination of the molecular weight of growth factor activity. A standard 12.5% polyacrilamide SDS slab gel was prepared. Ten percent glycerol and 2% SDS were added to the pooled fractions. Fifty percent of the sample was treated with 2.5% 2-mercaptoethanol. The remainder 50% was not exposed to 2-mercaptoethanol or other reducing agents. The samples and prestained molecular weight markers were then incubated for 3 min at 37° C. and electrophoresed overnight at a current of 10 mA. When the electrophoresis was completed, the gel was briefly rinsed in PBS and the distance of the molecular weight markers from the top of the gel was immediately meaured. Twenty-one half centimeter horizontal slices were then cut with a razor blade both from the lanes run under reducing and those run under non-reducing conditions. Slices were then washed twice with 1 ml of PBS and then shaken overnight at 4° C. in individual tubes containing 500 μl of 0.2% gelatin in PBS for elution of the biological activity. The gel slices were then removed from the tubes, which were then centrifuged in order to remove particulate material. The supernatants were transferred to new tubes. Twenty microliter aliquots from each fraction were tested for biological activity on endothelial cells.

A single peak of bioactivity was observed in the group not exposed to 2-mercaptoethanol. The apparent molecular weight, as assessed by comparing the position of the molecular weight markers to that of the slices, was about 43,000. No bioactivity was recovered from slices exposed to 2-mercaptoethanol.

These results gave a good assessment of the molecular weight of the growth factor, which has been confirmed with the molecule purified to homogeneity, and also indicated that its activity is abolished by reducing agents.

EXAMPLE 1

Culture of Follicular Cells and Media Collection

Primary cultures of bovine pituitary FC were established as previously described (20,41). In one embodiment in the culturing the 20% fetal bovine serum in reference 20 was reduced to 10%. Concentrations of 5 to 20% should be effective. Also no DNAase is used. All other components are the same. At confluency, cells were passaged into large scale tissue culture plates in the presence of low glucose Dulbecco's modified Eagle's medium (DMEM) supplemented with 10% fetal bovine serum, 2 mM glutamine and antibiotics. Shortly after reaching confluency the cultures were extensively washed with PBS in order to remove serum components. The cells were then incubated in a serum-free medium consisting of DMEM plus transferrin (10 μl/ml), insulin (5 μg/ml), selenium ($10^{-8}$ M), 2 mM glutamine and antibiotics. After three or four days, the medium was collected and replaced with fresh serum free medium. The collected medium was centrifuged (1000 g, 15 min. at 4° C.) and stored at −70° C. The conditioned medium (CM) was then collected every three or four days for up to six weeks.

EXAMPLE 2

Concentration of Conditioned Medium

Four to six liter batches of conditioned medium (CM) were subjected to ammonium sulfate precipitation. Ammonium sulfate (500 g/L) was added under constant stirring, until the salt was completely in solution. After 8–12 hours in the cold room, the material was centrifuged (20,000×g, 45 min at 4° C.). The supernatant was discarded and the pellet was resuspended with 10 mM Tris/Cl, pH 7.2, 50 mM NaCl and dialyzed at 4° C. against the same buffer for 8–12 h. The final volume was 50–60 fold less than the original.

Alternatively, the CM is concentrated using ultrafiltration using an Amecon stir cell (2.5 liter unit) using a membrane having a molecular weight cut off of 10,000 daltons with similar results.

EXAMPLE 3

Heparin-Sepharose Affinity Chromatography

The concentrated CM was applied to a H-S column (14) (10 ml) preequilibrated with 10 mM Tris/Cl, pH 7.2, 50 mM NaCl. The column was then washed with the same buffer until the absorbance at 280 nm was negligible and then eluted stepwise with 10 mM Tris/Cl pH 7.2 containing 0.15, 0.9 nd 3 M NaCl. The flow rate was 1.5 ml/min. Fractions of 1.5 ml were collected and aliquots, diluted with 0.2% gelatin in PBS, were tested for mitogenic activity on endothelial cells.

EXAMPLE 4

Reverse Phase HPLC (a) The most bioactive H-S fractions (0.9 M NaCl pool) were diluted fourfold with 0.1% trifluoroacetic acid (TFA) in water and applied to a Vydac C4 HPLC column (10×250 mm) preequilibrated in 0.1 TFA/20% acetonitrile. The column was eluted with a linear gradient of acetonitrile (20–45% in 115 min) at a flow rate of 2 ml/min. The absorbance was monitored at 21 nm. Fractions of 2 ml were diluted in 0.2% gelatin in PBS for assay on endothelial cells.

(b) The most bioactive fractions were pooled, diluted two fold in 0.1% TFA water and applied to a Vydac C4 HPLC column (4.6×250 mm) preequilibrated in 0.1% TFA/20% 2-propanol. The column was eluted with a linear gradient of 2-propanol (20–45% in 113 min). The flow rate was 0.6 ml/min. Aliquots of fractions were diluted for bioassays. The remainder of fractions were dried in a Speed-Va for SDS/PAGE (29) and structural analysis.

EXAMPLE 5

Bioassays

Bovine adrenal cortex or brain-derived capillary endothelial cells, adult or fetal bovine aortic endothelial cells, human umbilical vein endothelial cells, bovine corneal endothelial cells, adrenal cortex cells, lens epithelial cells, BHK-21 fibroblasts and human keratynocytes were cultured and maintained as previously described (17,47,48,50,51,52, 26,53). For bioassay, cells were seeded in the presence of their respective growth media at the density of $2 \times 10^4/35$ mm dish or $1 \times 10^4$/well in 12 multiwell plates. Fractions were added to cells in 5 μl/ml aliquots. After 4 or 5 days, cells were dissociated by exposure to trypsin and counted in a Coulter counter.

EXAMPLE 6

Protein Microsequencing

Approximately 20 pmol of protein from the most bioactive fractions obtained from the second C4 step were applied directly to a gas phase protein sequenator Model 470A (Applied Biosystems). Edman degradation cycles were carried out and identification of amino acid derivatives was made by an on line HPLC column (54).

Expression

Purification of growth factors is also described in U.S. Pat. Nos. 4,708,948; 4,376,071; 4,350,687; 4,444,760; and 4,722,998.

The recombinant DNA production of growth factors is described in U.S. Pat. Nos. 4,670,394; 4,721,672; 4,738,927; 4,783,412; and 4,801,542; all of which are incorporated herein by reference.

It is anticipated that the growth factors described herein will be able to be cloned and produced according to the methods described in the patents and references described herein.

It is understood that the growth factor described herein may be either the dimer (43,000 to 46,000 kDa) or the monomer (about 23 kDa).

While only a few embodiments of the invention have been shown and described herein, it will be come apparent to those skilled in the art that various modifications and changes can be made in the present invention to the novel endothelial cell growth factor, its methods of isolation, manufacture using recombinant DNA methods and its uses in therapy (wound healing) without departing from the spirit and scope of the present invention. All such modification and changes coming within the scope of the appended claims are intended to be carried out thereby.

We claim:

1. A method of promoting the proliferation of human endothelial cells in vitro, which method comprises:
    administering to such human cells an effective amount of isolated and purified human endothelial cell growth factor wherein said endothelial cell growth factor comprises a protein which is obtained from human folliculi stellate cells and which is in the form of a dimeric protein having a molecular weight of approximately 43–45 kd as determined by SDS PAGE, under nonreducing condition.

2. The method of claim 1, wherein the human endothelial cells are grown in cell culture.

3. A method of promoting the proliferation of human endothelial cells in vivo which comprises;
    a) administering to a wound a pharmaceutical composition comprising human endothelial cell growth factor which comprises a protein which is obtained human folliculi stellate cells and which is in the form of a dimeric protein having a molecular weight of approximately 43–45 kd as determined by SDS PAGE, under nonreducing conditions which isolated factor has endothelial cell growth factor activity which factor comprises at its N-terminus the amino acid sequence Ala-Pro-Met-Ala-Glu-Gly-Gly-Gln-Lys-Pro-His-Glu, and
    a pharmaceutically-acceptable carrier,
    wherein
    said growth factor is present in said composition in a concentration of between about 10 picogram/milliliter and about 500 picogram/milliliter.

4. A method of promoting the proliferation of human endothelial cells in vivo, which method comprises:
    (a) administering an isolated and purified endothelial cell growth factor wherein
    said endothelial cell growth factor is a protein obtained from human folliculi stellate cells in the form of a dimeric protein having a molecular weight of approximately 43–45 kd which protein is obtained by SDS PAGE under non-reducing conditions.

5. The method of claim 4 wherein said protein is administered in vivo in between about 10 picogram/ml and 500 picogram/ml.

6. The method of claim 4 wherein said purified human endothelial cell growth factor forms two substantially homologous units each having a molecular weight of about 23 kd.

7. The method of claim 4 wherein for the isolated and purified human endothelial cell growth factor has at its N-terminus the amino acid sequence Ala-Pro-Met-Ala-Glu-Gly-Gly-Gln-Lys-Pro-His-Glu-.

8. The method of claim 4 wherein in step (a) the protein is present as a pharmaceutical composition which comprises a pharmaceutically-acceptable carrier.

9. The method of claim 4 wherein said isolated and purified human endothelial cell growth factor has an N-terminus amino acid sequence of -Ala-Pro-Met-Ala-Glu-Gly-Gly-Gln-Lys-Pro-His-Glu-Val-Val-Lys-Phe-Met-Asp-Val-Tyr-Gln-(Arg)-Ser-Phe-X-Arg-Pro-Ile-Glu-Thr-Leu-(Val)-X-Ile-X-(Gln)-Glu-Tyr-(Pro)- wherein the amino acids in parenthesis are uncertain and the -X indicates an amino acid of unknown identity.

10. The method of claim 8 for promoting the proliferation of human endothelial cells in vivo, wherein the pharmaceutically acceptable carrier is selected from saline, dextrose, or carbopol.

11. The method of claim 8 wherein the protein is present as a pharmaceutical composition which comprises a parenteral pharmaceutically-acceptable carrier.

12. The method of claim 8 wherein in subpart (a) said protein is administerined in at least one application of between about 50 microgram/ml and 1000 microgram/ml.

13. The method of claim 8 wherein said purified human endothelial cell growth factor is formed of two substantially homologous units each having a molecular weight of about 23 kd.

14. The method of claim 8 wherein said protein is a human protein source and comprises at its N-terminus the partial amino acid sequence Ala-Pro-Met-Ala-Glu-Gly-Gly-Gln-Lys-Pro-His-Glu-.

15. The method of claim 8 wherein said human protein has an N-terminus partial amino acid sequence of -Ala-Pro-Met-Ala-Glu-Gly-Gly-Gln-Lys-Pro-His-Glu-Val-Val-Lys-Phe-Met-Asp-Val-Tyr-Gln-(Arg)-Ser-Phe-X-Arg-Pro-Ile-Glu-Thr-Leu-(Val)-X-Ile-X-(Gln)-Glu-Tyr-(Pro)- wherein the amino acids in parenthesis are uncertain and the -X indicates an amino acid of unknown identity.

* * * * *